US012758173B2

(12) United States Patent
Ma et al.

(10) Patent No.: US 12,758,173 B2
(45) Date of Patent: Oct. 13, 2026

(54) VASCULAR IMAGING METHODS, SYSTEMS, AND MEDIUMS

(71) Applicant: SHANGHAI UNITED IMAGING HEALTHCARE CO., LTD., Shanghai (CN)

(72) Inventors: Canzhen Ma, Shanghai (CN); Weilong Mao, Shanghai (CN); Huikai Liu, Shanghai (CN); Jun Xiang, Shanghai (CN); Hui Yin, Shanghai (CN); Jianqing Sun, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 18/955,891

(22) Filed: Nov. 21, 2024

(65) Prior Publication Data

US 2025/0160777 A1 May 22, 2025

(30) Foreign Application Priority Data

Nov. 21, 2023 (CN) ......................... 202311561263.5

(51) Int. Cl.

*A61B 6/50* (2024.01)
*A61B 6/00* (2024.01)
*A61B 6/02* (2006.01)

(52) U.S. Cl.

CPC .............. *A61B 6/504* (2013.01); *A61B 6/027* (2013.01); *A61B 6/4441* (2013.01); *A61B 6/481* (2013.01); *A61B 6/54* (2013.01)

(58) Field of Classification Search

CPC ......... A61B 6/027; A61B 6/481; A61B 6/504; A61B 6/4441

See application file for complete search history.

(56) References Cited

U.S. PATENT DOCUMENTS

| | | | | |
|---|---|---|---|---|
| 5,412,702 | A | 5/1995 | Sata | |
| 2008/0037700 | A1 | 2/2008 | Grass et al. | |
| 2010/0014740 | A1 | 1/2010 | Movassaghi et al. | |
| 2011/0037761 | A1 * | 2/2011 | Mistretta | G06T 11/008 600/431 |
| 2011/0206259 | A1 | 8/2011 | Mistretta et al. | |
| 2016/0007949 | A1 * | 1/2016 | Kobayashi | A61B 6/54 378/42 |
| 2017/0000428 | A1 * | 1/2017 | Goto | A61B 6/54 |
| 2017/0124732 | A1 * | 5/2017 | Proksa | A61B 6/032 |

(Continued)

FOREIGN PATENT DOCUMENTS

| | | | |
|---|---|---|---|
| CN | 111528881 A | 8/2020 | |
| WO | WO-2010046839 A1 * | 4/2010 | A61B 6/027 |

OTHER PUBLICATIONS

Lessin Barry D. et al., Helical CT Angiography a Diagnostic Problem Solving Technique, Clinical Imaging, 18(1): 59-64, 1994.

(Continued)

*Primary Examiner* — Carolyn A Pehlke
(74) *Attorney, Agent, or Firm* — METIS IP LLC

(57) ABSTRACT

Embodiments of the present disclosure provide vascular imaging methods, systems, and storage mediums. The vascular imaging method may include obtaining imaging data of a target object, the imaging data being obtained through a spiral scanning manner, and generating a vascular angiographic image based on the imaging data.

17 Claims, 13 Drawing Sheets

(56) References Cited

U.S. PATENT DOCUMENTS

| | | | | |
|---|---|---|---|---|
| 2017/0135651 | A1* | 5/2017 | Kugler .................. | A61B 6/482 |
| 2022/0061791 | A1* | 3/2022 | Vaz ........................ | A61B 6/504 |
| 2025/0367474 | A1 | 12/2025 | Owens et al. | |

OTHER PUBLICATIONS

Hatamikia S et al., Source-detector trajectory optimization in cone-beam computed tomography: a comprehensive review on today's state-of-the-art, Physics in Medicine & Biology, 67(16): 1-22, 2022.

Schomberg Hermann, Complete Source Trajectories for C-Arm Systems and a Method for Coping with Truncated Cone-Beam Projections, Porceedings of the Fully3D Conference, 2001, 4 pages.

The Partial European Search Report in European Application No. 24214517.5 mailed on Mar. 26, 2025, 13 pages.

First Office Action in Chinese Application No. 202311561263.5 mailed on Nov. 5, 2025, 13 pages.

* cited by examiner

1000

VASCULAR IMAGING METHODS, SYSTEMS, AND MEDIUMS

CROSS-REFERENCE TO RELATED APPLICATIONS

This application claims priority to Chinese application No. 202311561263.5 filed on Nov. 21, 2023, the entire contents of which are incorporated herein by reference.

TECHNICAL FIELD

The present disclosure relates to the field of medical technology, and in particular, to vascular imaging methods, systems, and mediums.

BACKGROUND

Digital subtraction angiography (DSA) is a medical imaging technique that may be used to evaluate and diagnose lesions or abnormalities in the vascular system. DSA performs, by injecting a contrast agent (e.g., iodide) into a body of a patient, continuous image acquisition using an X-ray device. The captured images may be used to detect and diagnose various vascular diseases (e.g., arterial stenosis, thrombosis, aneurysms, etc.), which helps physicians well determine a position, a severity, and a blood flow of the lesion to guide subsequent treatment plans.

Therefore, some embodiments of the present disclosure provide vascular imaging methods, systems, and mediums.

SUMMARY

One of the embodiments of the present disclosure provides a vascular imaging method. The vascular imaging method may include obtaining imaging data of a target object. The imaging data may be obtained through a spiral scanning manner. The vascular imaging method may further include generating a vascular angiographic image based on the imaging data.

In some embodiments, the imaging data may be obtained through the spiral scanning manner by obtaining the imaging data by receiving, through a radiation detector, radiations emitted by a radiation emitter when the radiation emitter is moving along a first direction and rotate around the first direction at the same time.

In some embodiments, the vascular imaging method may be applied to an X-ray imaging device. The X-ray imaging device may include an arm, a radiation emitter and a radiation detector respectively disposed at two ends of the arm. The vascular imaging method may further include obtaining the imaging data through the spiral scanning manner using the radiation emitter and the radiation detector at the two ends of the arm.

In some embodiments, the obtaining the imaging data may include controlling the arm to move along a first direction and the radiation emitter to rotate around the first direction at the same time, and obtaining the imaging data by receiving radiations emitted by the radiation emitter through the radiation detector.

In some embodiments, the obtaining the imaging data may include controlling the arm to move along the first direction and the radiation emitter to perform a first rotation around the first direction at the same time, controlling the radiation emitter to emit first radiations, obtaining first imaging data by receiving the first radiations through the radiation detector, in response to determining that an angle of the first rotation is greater than a preset angle, stopping the first rotation, controlling the arm to move along the first direction and the radiation emitter to perform a second rotation around the first direction at the same time, controlling the radiation emitter to emit second radiations, obtaining second imaging data by receiving the second radiations through the radiation detector, wherein a rotation direction of the second rotation is opposite to a rotation direction of the first rotation, and determining the imaging data based on the first imaging data and the second imaging data.

In some embodiments, an ending point position of the first rotation may be a starting point position of the second rotation.

In some embodiments, the obtaining the imaging data through the spiral scanning manner using the radiation emitter and the radiation detector at the two ends of the arm may include controlling the arm to move from a scan starting point along a first direction and the radiation emitter to rotate around the first direction at the same time, controlling the radiation emitter to emit first radiations, obtaining first imaging data by receiving the first radiations through the radiation detector, controlling the radiation emitter to stop emitting the first radiations and the arm to return to the scan starting point, controlling the arm to move from the scan starting point along a second direction and the radiation emitter to rotate around the second direction at the same time, controlling the radiation emitter to emit second radiations, obtaining second imaging data by receiving the second radiations through the radiation detector, wherein the first direction and the second direction may be opposite, and determining the imaging data based on the first imaging data and the second imaging data.

In some embodiments, the scan starting point may be a non-endpoint position in a scan range.

In some embodiments, the arm may be connected to a frame, and the frame may drive the arm to move. A rotation of the arm may be achieved through at least one of: the arm rotating at a connection relative to the frame; or the connection between the frame and the arm remaining stationary relative to the arm, and the frame driving the arm to rotate.

In some embodiments, the arm rotating at the connection relative to the frame may include a bearing being disposed at the connection, and the arm rotating relative to the frame through the bearing; or the connection between the frame and the arm being equipped with a slide rail, and the arm sliding relative to the frame along the slide rail.

In some embodiments, the connection between the arm and the frame may be at a center position of the arm; or the connection between the arm and the frame may be offset from the center position of the arm, and the radiation emitter and the radiation detector may rotate relative to the arm.

In some embodiments, the movement of the radiation emitter is achieved through at least one of drive the frame to move the arm; or the arm being equipped with a slide rail, and the slide rail moving relative to the arm.

In some embodiments, the injection of the contrast agent into the blood vessel of the target object may be performed simultaneously or alternately with the spiral scanning manner of the radiation emitter and the radiation detector.

In some embodiments, the injection of the contrast agent into the blood vessel of the target object being performed alternately may include the spiral scanning time period of the spiral scanning partially overlapping with the injection time period of the contrast agent.

In some embodiments, the generating the vascular angiographic image based on the imaging data may include obtaining a reconstructed image by performing rapid reconstruction based on the imaging data, and generating the vascular angiographic image by performing a vascular segmentation on the reconstructed image.

In some embodiments, the spiral scanning manner includes at least a first sub-scanning and a second sub-scanning, and injection of the contrast agent includes at least a first injection and a second injection; wherein a start time of the first sub-scanning is later than a start time of the first injection, and an end time of the first sub-scanning is later than an end time of the first injection; and a start time of the second sub-scanning is later than a start time of the second injection, and an end time of the second sub-scanning is later than an end time of the second injection.

In some embodiments, the generating the vascular angiographic image based on the imaging data may include obtaining auxiliary imaging data, generating an image sequence based on the imaging data and the auxiliary imaging data, and generating the vascular angiographic image based on the two-dimensional image sequence.

In some embodiments, the vascular imaging method may further include obtaining a first speed and a second speed based on a preset corresponding relationship, controlling the arm to move along the first direction at the first speed, and controlling the radiation emitter to rotate around the first direction at the second speed. The preset corresponding relationship may include a mapping relationship between the first speed of the arm moving along the first direction and the second speed of the radiation emitter rotating around the first direction.

In some embodiments, the obtaining the first speed and the second speed based on the preset corresponding relationship may include determining a scan range based on a scan plan of the target object, determining a movement mode of the arm based on the scan range, determining a query target from the preset corresponding relationship based on the movement mode of the arm, and determining the first speed and the second speed based on the query target.

In some embodiments, the vascular imaging method is performed via digital subtraction angiography (DSA).

One of the embodiments of the present disclosure provides a vascular imaging system. The vascular imaging system may further include a processor configured to obtain imaging data of a target object, the imaging data being obtained through a spiral scanning manner, and generate a vascular angiographic image based on the imaging data.

One of the embodiments of the present disclosure provides a vascular imaging system. The vascular imaging system may further include an imaging data obtaining module configured to obtain imaging data of a target object including a contrast agent, the imaging data being obtained through a spiral scanning manner; and an imaging module configured to generate a vascular angiographic image based on the imaging data.

One of the embodiments of the present disclosure provides a non-transitory computer-readable storage medium including executable instructions. When read by at least one processor, the executable instructions may cause the at least one processor to perform a vascular imaging method. The vascular imaging method may include obtaining imaging data of a target object, the imaging data being obtained through a spiral scanning manner; and, and generating a vascular angiographic image based on the imaging data.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
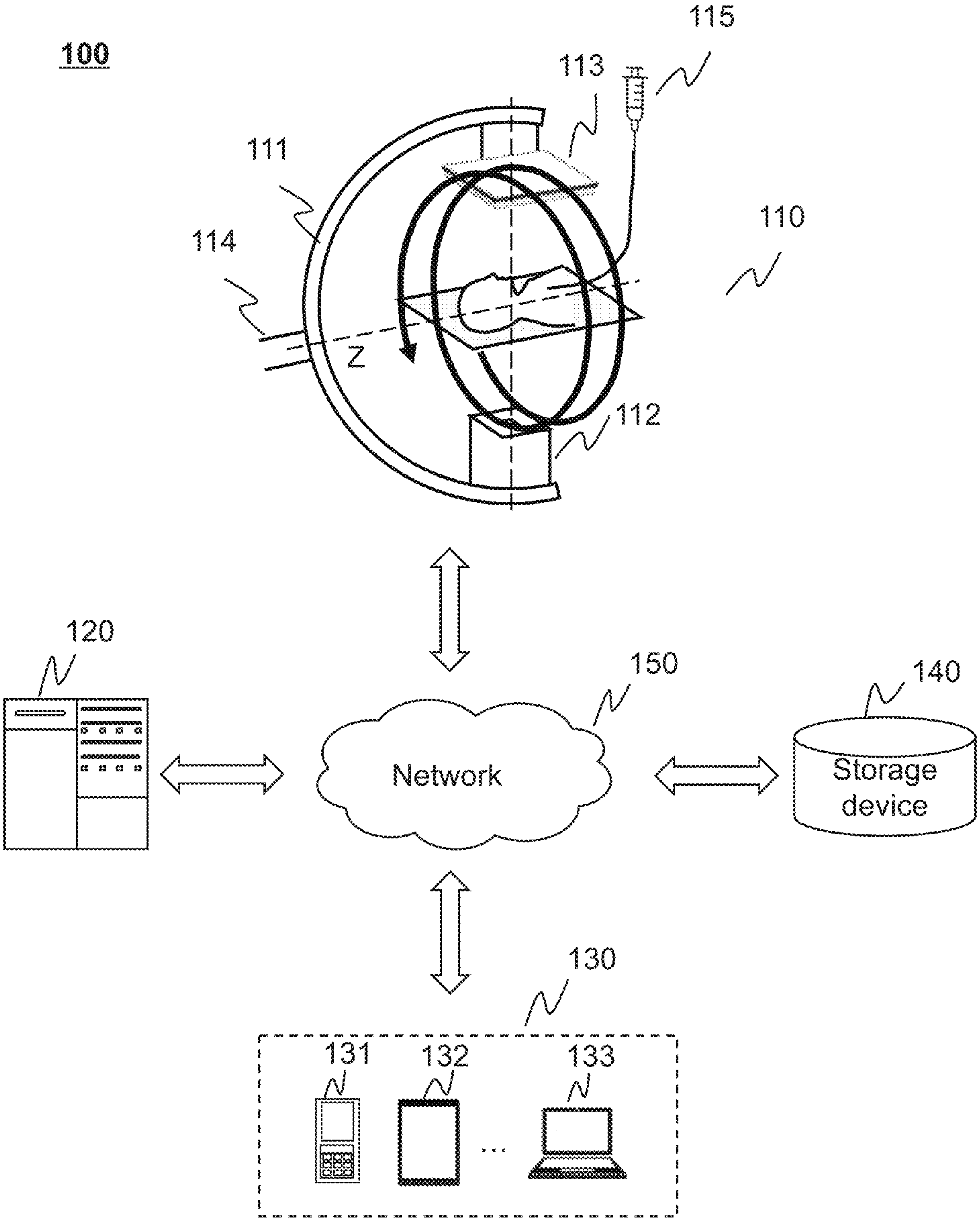
FIG. 1 is a schematic diagram of an application scenario of a vascular imaging system according to some embodiments of the present disclosure.

In order to more clearly illustrate the technical solutions relating to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

It should be understood that the "system," "device," "unit," and/or "module" used herein are one method to distinguish different components, elements, parts, sections, or assemblies of different levels. However, if other words may achieve the same purpose, the words may be replaced by other expressions.

As used in the disclosure and the appended claims, the singular forms "a," "an," and "the" include plural referents unless the content clearly dictates otherwise; the plural forms may be intended to include singular forms as well. In general, the terms "comprise," "comprises," and/or "comprising," "include," "includes," and/or "including," merely prompt to include steps and elements that have been clearly identified, and these steps and elements do not constitute an exclusive listing. The methods or devices may also include other steps or elements.

The flowcharts used in the present disclosure illustrate operations that the system implements according to the embodiment of the present disclosure. It should be understood that the foregoing or following operations may not necessarily be performed exactly in order. Instead, the operations may be processed in reverse order or simultaneously. Besides, one or more other operations may be added to these processes, or one or more operations may be removed from these processes.

In some cases, computed tomography angiography (CTA) may be performed by a computed tomography (CT) device. In the preoperative detection stage, the CTA may complete a CT scan through intravenous injection of a contrast agent, and reconstruct three dimensional (3D) images of blood vessels in a long-axial range. Physicians are assisted in diagnosing head and neck vascular diseases, cardiovascular diseases, and peripheral vascular diseases. However, in the diagnostic and treatment process, the CTA examination consumes a lot of time and delays the diagnosis and treatment of the patient. At the same time, the radiation of the CTA examination has a non-negligible side effect.

CT angiography (CTA) is widely used in the diagnosis of vascular diseases by virtue of the advantages of wide range, rapid scanning, non-invasive, and easy operation, thereby providing an important diagnostic basis for vascular variations and vascular diseases. However, intravenous injection brings non-specific problems for CTA. For example, after the intravenous injection, the contrast agent may enter into a left side of the heart, to the lung, back to the heart, and to the brain. During the intravenous injection, a blood vessel of the artery may not be seen alone. However, many blood vessels that are not related to the artery may be shown, and these blood vessels may be called non-specific. That is, the intravenous injection may introduce some unnecessary blood vessels to cause interference. CTA is a medical imaging diagnostic technology, and CTA examination consumes a lot of time for acute patients in the diagnostic and treatment process. Therefore, it is desirable to realize the acquisition of vascular images, diagnosis, and treatment in a single session at a treatment site (e.g., a catheterization laboratory).

Three-dimensional digital subtraction angiography (3D-DSA) is an advanced digital angiography technique that combines conventional digital subtraction angiography (DSA) with 3D reconstruction. 3D-DSA converts, by acquiring multiple 2D-DSA images in succession, these images into a stereoscopic 3D blood vessel model using a computer reconstruction algorithm. Compared with traditional 2D-DSA, 3D-DSA provides more comprehensive and intuitive information about the structure of the blood vessel. With 3D-DSA, physicians may rotate, scale, and move the vascular model to view the vascular system from all angles and perspectives, which helps physicians better assess a position, shape, size, and distribution of vascular lesions to make an accurate diagnosis and develop a treatment plan.

In practical applications (e.g., diagnosis and treatment of stroke), a physician wants to see long-range 3D vascular images from the aortic arch to the cranial roof. The X-ray imaging device (e.g., cone-beam computed tomography (CBCT)) has the functions of two-dimensional (2D) angiography and three-dimensional angiography through digital subtraction angiography (DSA). During DSA, the contrast agent may be usually injected through the artery. Taking intracranial angiography as an example, 3D-DSA completes 3D vascular imaging of the hemisphere in an axial direction of about 18 cm after cannulation of the internal carotid artery, which is used to diagnose aneurysm or vascular stenosis during the operation, and to evaluate the effect of interventional therapy after the operation. The DSA device is the gold standard for the diagnosis of many vascular diseases and is a key imaging device in interventional therapy. However, an intrinsic scanning range of the current DSA is small (e.g., 17 cm-18 cm), the total coverage of the imaging data of the current DSA device is small, the reconstructed 3D vascular range is small, and intracranial imaging needs to be performed multiple times on vascular imaging of the whole brain, and the 3D vascular imaging from the aortic arch to the cranial roof cannot be accomplished directly.

Soft tissue imaging in the long-axial range may be achieved by the spiral scanning manner with an X-ray imaging system. However, the current CBCT has a low soft tissue contrast resolution, and the scanning is time-consuming, so the long-axial tomography lacks clinical application value.

The contrast agent is injected by a high-pressure injector through the artery, and spreads along the artery with the bloodstream. The continuously injected contrast agent gradually fills the blood vessel and enters the capillaries and the veins, and the angiography of arterial vascular imaging has a limited validity period and the scan duration of the imaging device is limited. The conventional long-axial-range spiral scanning scheme does not take into account key factors (e.g., an amount of usage of contrast agent/injection rate, a diffusion time of contrast agent, etc.), and cannot be applied to long-range vascular imaging.

Therefore, some embodiments of the present disclosure provide vascular imaging methods, systems, and mediums. In an X-ray imaging system (e.g., a C-arm X-ray imaging system, e.g., DSA device), X-ray imaging data may be performed in a spiral scanning manner by injecting the contrast agent. A three-dimensional vascular image in a long-axial range may be accomplished by performing the rapid and accurate reconstruction based on the imaging data. The vascular imaging method according to some embodiments of the present disclosure eliminates the preoperative CT examination process. For example, in the preoperative imaging diagnostic process, the preoperative diagnostic process may include taking a CT and a contrast-enhanced CT (e.g., CTA), which may be used under a CT device for angiography. The vascular imaging method according to some embodiments of the present disclosure makes all diagnosis and treatment procedures completed directly in the catheterization laboratory, which greatly shortens the diagnosis and treatment process, improves the success rate of rescue, and reduces the radiation dose at the same time. In addition, compared with the 3D-DSA vascular imaging method, the vascular imaging method according to some embodiments of the present disclosure has a larger scan range, and 3D vascular imaging from the aortic arch to the cranial roof may be accomplished directly with a smaller radiation dose and contrast agent dose and a shorter scan duration. Compared to CT devices, DSA devices may provide better imaging quality (e.g., a higher resolution), so it is necessary to achieve imaging with DSA devices in a long axial range.

It should be noted that the above examples are provided merely for the purpose of illustration, and not intended to limit the application device of the imaging method disclosed in the present disclosure. For example, the disclosed imaging method may be applied to DSA device, computed tomography (CT) device, etc.

FIG. 1 is a schematic diagram of an application scenario of a vascular imaging system according to some embodiments of the present disclosure.

As shown in FIG. 1, the application scenario 100 of the vascular imaging system may include an X-ray imaging device 110 (e.g., DSA device), a processor 120, a terminal device 130, a storage device 140, and a network 150.

The X-ray imaging device 110 may be configured to obtain scanning data of a target object by scanning the target object within a detection region or a scanning region.

In some embodiments, the X-ray imaging device 110 may include an arm 111, a radiation emitter 112, a radiation detector 113, a frame 114, and a high-pressure injector 115. The radiation emitter 112 and the radiation detector 113 may be respectively disposed at two ends of the arm 111.

The arm 111 is a main structural portion of the X-ray imaging device 110. For example, as shown in FIG. 1, the arm 111 is a C-shaped arm. The arm 111 may be flexibly rotated and moved around the target object (e.g., a patient) during a surgical or diagnostic procedure, thereby providing many scanning angles and a large scan range.

The radiation emitter 112 refers to a component that generates scanning rays, such as X-rays. Taking the radiation emitter that generates X-rays as an example, the radiation emitter may mainly include a high-voltage generator and an X-ray tube. The high-voltage generator may be responsible for providing a high voltage to accelerate electrons. The X-ray tube may serve as a place for the electrons to hit a metal target to produce X-rays.

The radiation detector 113 may be configured to receive radiations generated by the radiation emitter 112.

The frame 114 refers to a frame structure that supports and fixes a component such as the arm 111, the radiation emitter 112, the radiation detector 113, etc.

In some embodiments, the arm 111 may be connected to the frame 114, and the frame may drive the arm to move. The connection mode may include a mechanical joint, an electric control, a magnetic adsorption, a fixed connection, etc., which is not limited in the present disclosure.

In some embodiments, the movement of the radiation emitter may be achieved through at least one of driving the frame to move the arm or equipping the arm with a slide rail. The slide rail moves relative to the arm.

In some embodiments, the frame may be driven by a driving component to move the arm. The driving component includes a motor and a transmission element. The motor includes a DC motor, an AC motor, and a stepper motor, etc. The transmission element includes a gear, a belt, a chain, a drive shaft, etc.

The high-pressure injector 115 may be configured to inject a contrast agent. In some embodiments, the high-pressure injector 115 may mainly include a component such as an injector body, a high-pressure pump, etc. The injector body may be configured to load the contrast agent, and the high-pressure pump may be responsible for generating high pressure to push the contrast agent into the body of the patient.

The processor 120 may be configured to process data and/or information obtained from the X-ray imaging device 110, the terminal device 130, the storage device 140, and/or other components of the application scenario 100 of the vascular imaging system, and to analyze and/or process the data and/or information. For example, the processor 120 may obtain imaging data from the X-ray imaging device 110, and generate, based on the imaging data, a vascular angiographic image.

In some embodiments, the processor 120 may be a single server or a server group. The server group may be centralized or distributed. In some embodiments, the processor 120 may be local or remote. For example, the processor 120 may access information and/or data from the X-ray imaging device 110, the terminal device 130, and/or the storage device 140 via the network 150. As another example, the processor 120 may be directly connected to the X-ray imaging device 110, the terminal device 130, and/or the storage device 140 to access the information and/or data. In some embodiments, the processor 120 may be implemented on a cloud platform. For example, the cloud platform may include a private cloud, a public cloud, a hybrid cloud, a community cloud, a distributed cloud, an inter-cloud, a multi-cloud, or the like, or any combination thereof.

In some embodiments, the processor 120 and the X-ray imaging device 110 may be integrated. In some embodiments, the processor 120 and the X-ray imaging device 110 may be directly or indirectly connected to jointly realize the methods and/or functions described herein.

The terminal device 130 may communicate with and/or be connected to the X-ray imaging device 110, the processor 120, and/or the storage device 140. In some embodiments, interaction with a user may be achieved via the terminal device 130. In some embodiments, the terminal device 130 may include a mobile device 131, a tablet computer 132, a laptop computer 133, etc., or any combination thereof. In some embodiments, the terminal device 130 (or all or part of functions) may be integrated into the processor 120.

The storage device 140 may store data, instructions, and/or any other information. In some embodiments, the storage device 140 may store data (e.g., imaging data, etc.) obtained from the X-ray imaging device 110, the processor 120, and/or the terminal device 130. In some embodiments, the storage device 140 may store data and/or instructions used by the processor 120 to execute or accomplish the exemplary methods described in the present disclosure.

In some embodiments, the storage device 140 may include one or more storage components. Each storage component may be a stand-alone device or may be a part of another device. In some embodiments, the storage device 140 may include a random access memory (RAM), a read-only memory (ROM), a mass storage, a removable storage device, a volatile read-and-write memory, or the like, or any combination thereof. In some embodiments, the storage device 140 may be implemented on a cloud platform. In some embodiments, the storage device 140 may be a part of the X-ray imaging device 110, the processor 120, and/or the terminal device 130.

The network 150 may include any suitable network that may facilitate exchange of information and/or data. In some embodiments, at least one component (e.g., the X-ray imaging device 110, the processor 120, the terminal device 130, the storage device 140) of the application scenario 100 of the vascular imaging system may exchange information and/or data with at least one other component of the application scenario 100 of the vascular imaging system via the network 150. For example, the processor 120 may obtain imaging data, etc., from the X-ray imaging device 110 via the network 150.

It should be noted that the descriptions of the application scenario 100 of the vascular imaging system are merely provided for the purpose of illustration, and not intended to limit the scope of the present disclosure. For those skilled in the art, various modifications or variations may be made under the teachings of the present disclosure. For example, the application scenario 100 of the vascular imaging system may achieve similar or different functions on other devices, such as an X-ray imaging device having other shaped arms (e.g., an X-ray imaging device having an O-shaped arm). However, these variations and modifications do not depart from the scope of the present disclosure.

Figure 2:
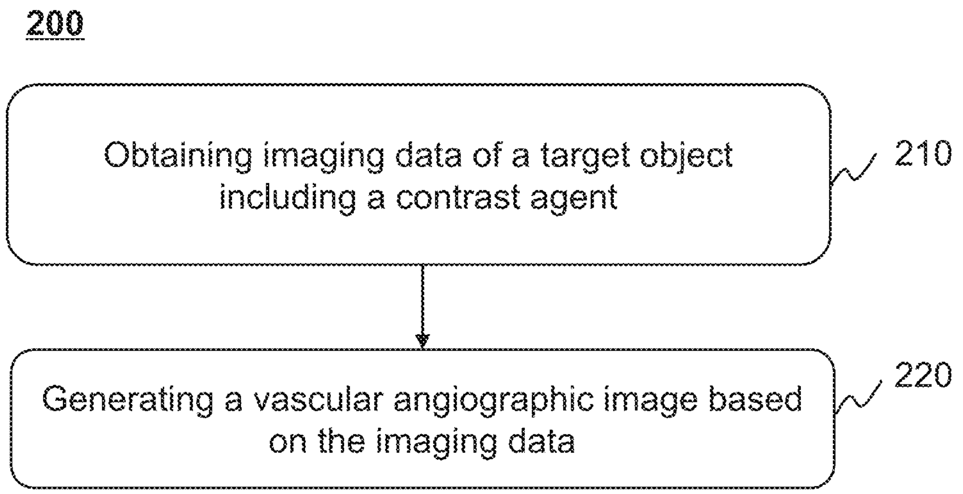
FIG. 2 is a flowchart illustrating an exemplary vascular imaging method according to some embodiments of the present disclosure.

FIG. 2 is a flowchart illustrating an exemplary vascular imaging method according to some embodiments of the present disclosure. In some embodiments, the process 200 may be executed by a processor (e.g., the processor 120).

In 210, imaging data of a target object including a contrast agent is obtained.

The target object refers to an object to be detected. For example, the target object may include a patient attending a clinic, a guest for a medical checkup, a patient for radiation therapy, etc. In some embodiments, the target object may include a specific portion of the body, such as a head, a chest, an abdomen, an arm, a leg, or the like, or any combination thereof. The target object including the contrast agent refers to injecting the contrast agent into the target object, and the contrast agent exists in the target object when obtaining the imaging data.

In some embodiments, the imaging data may be obtained through a spiral scanning manner.

In the spiral scanning manner, the scanning bed that supports the target object may not move. For example, during a spiral scanning manner of a surgery operation, since the target object relative to the X-ray scanning device is required to be stationary (e.g., when a status of the target object is detected through a catheter or a monitor device, the target object is required to be stationary), the scanning bed may not move.

In some embodiments, a time period of the spiral scanning manner and a time period for injecting the contrast agent into the blood vessel of the target object may overlap at least in part. For example, the spiral scanning manner may be started after the contrast agent is injected. As another example, the spiral scanning manner may also be started at the same time when the contrast agent is injected. As yet another example, the spiral scanning manner may be ended after an injection of the contrast agent is ended. Alternatively, the spiral scanning manner may be ended simultaneously with the injection of the contrast agent is ended. The processor may use imaging data corresponding to a moment when the spiral scanning manner is performed and the contrast agent exists in the blood vessel as the imaging data of the target object that is obtained.

In some embodiments, the processor may perform the spiral scanning by making a radiation emitter move along a first direction and rotate around the first direction at the same time, by controlling a medical scanning device (e.g., the X-ray imaging device 110), and obtain the imaging data by receiving radiations emitted by the radiation emitter through a radiation detector.

In some embodiments, the injection of the contrast agent into the blood vessel of the target object may be performed simultaneously or alternately with the spiral scanning manner of the radiation emitter and the radiation detector.

Figure 12:
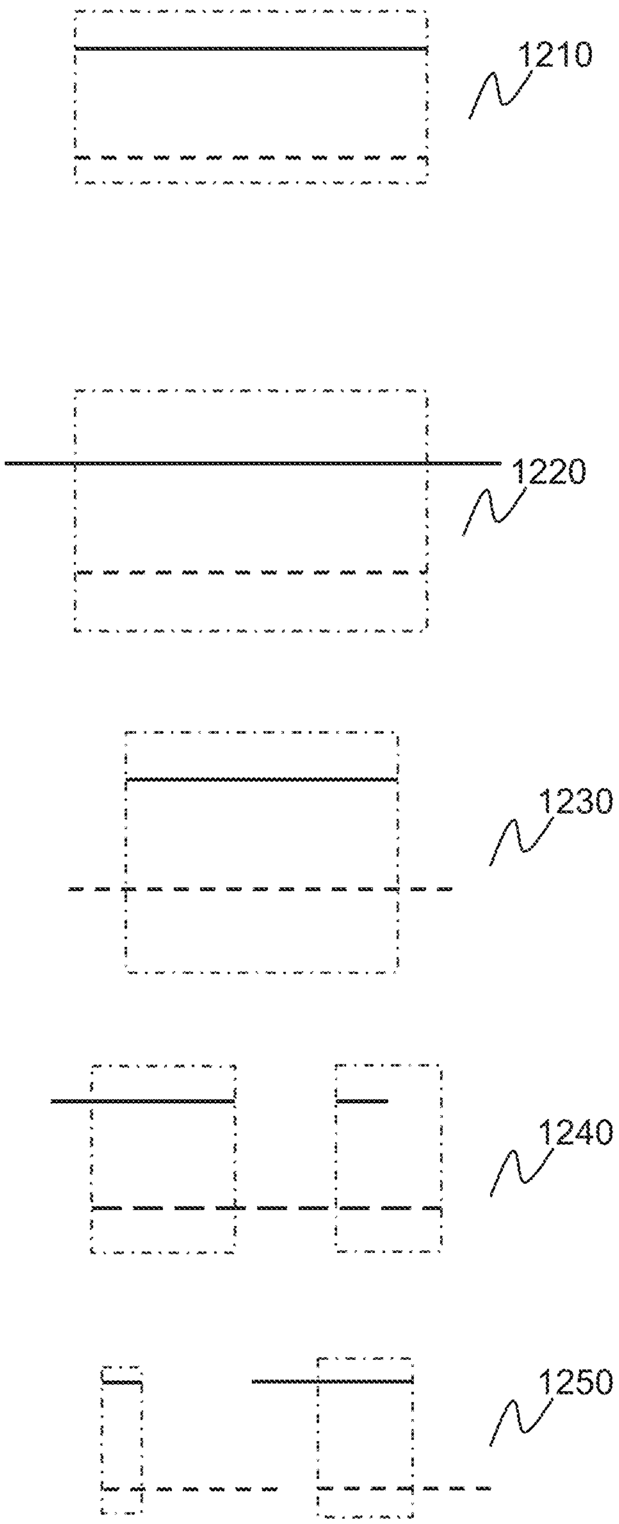
FIG. 12 is an exemplary schematic diagram of a corresponding relationship between an injection time period of a contrast agent and a time period of a spiral scanning manner according to some embodiments of the present disclosure.

FIG. 12 is an exemplary schematic diagram of a corresponding relationship between an injection time period of a contrast agent and a time period of a spiral scanning manner according to some embodiments of the present disclosure.

1210, 1220, 1230, 1240, and 1250 may represent some or all of a scan flow in a single imaging process, respectively. The solid line represents the injection time period of the contrast agent, along the direction indicated by the arrow, the starting point of the solid line indicates the start time of contrast agent injection, and the end point indicates the stop time of contrast agent injection. The dotted line represents the time period of the spiral scanning manner, the start of the dashed line represents the start scanning time of the spiral scanning, and the end point represents the stop scanning time of the spiral scanning. The dotted and dashed line represents an overlap (indicates that contrast agent injection and spiral scanning were performed simultaneously during this time period) between the injection time period of the contrast agent and the time period of the spiral scanning manner. In 1210, the injection time period of the contrast agent is equal to the time period of the spiral scanning manner, which corresponds to a case that the injection of the contrast agent and the spiral scanning manner are simultaneously performed. In 1220, 1230, 1240, and 1250, the injection time period of the contrast agent overlaps at least partially with the time period of the spiral scanning manner. 1220 indicates that the start time of the contrast agent injection is earlier than the start time of the spiral scanning, and the stop time of the contrast agent injection is earlier than the stop time of the spiral scanning. 1230 indicates that a start time of the contrast agent injection is earlier than a start time of the spiral scanning, and a stop time of the contrast agent injection is later than a stop time of the spiral scanning. 1240 indicates that a plurality of sub-scanning processes are included in a single imaging process with the injection time period of the contrast agent being non-continuous and the time period of the spiral scanning manner being continuous. 1250 indicates that a plurality of sub-scanning processes are include in a single imaging process with the injection time period of the contrast agent being non-continuous, and the time period of the spiral scanning manner also being non-continuous.

It should be noted that the above example is merely provided for the purpose of illustration. For example, 1210 may be considered a special case (e.g., a case in which the time period of the spiral scanning manner overlaps wholly with the injection time period of the contrast agent) of a case in which the time period of the spiral scanning manner overlaps at least partially with the injection time period of the contrast agent. As another example, when the plurality of sub-scanning processes are included in a single imaging process, the injection time period of the contrast agent may be continuous, and the time period of the spiral scanning manner may be non-continuous (not shown).

In some embodiments, a spiral scanning time period of the spiral scanning manner may be greater than an injection time period of the contrast agent, or the injection time period of the contrast agent may be greater than the spiral scanning time period of the spiral scanning manner. For example, if the injection time period of the contrast agent is greater than the time period of spiral scanning manner, the injection time point of the contrast agent may be earlier than a start time of the spiral scanning manner, and the contrast agent may be injected continuously during the time period of spiral scanning manner.

The injection of the contrast agent and the spiral scanning manner being performed alternately may include the time period of the spiral scanning manner partially overlapping with the injection time period of the contrast agent. For example, the time period of the spiral scanning manner and the injection time period of the contrast may overlap over a period of 2.4 s to 7.2 s shown in FIG. 3B.

The contrast agent refers to a substance used in medical examinations and diagnosis that is usually injected, taken orally, or otherwise introduced into the interior of the body. By injecting the contrast agent into the blood vessel, a contrast of the blood vessel in imaging such as X-rays and CT scans may be increased. In some embodiments, the contrast agent may include sodium iodide, iodate, etc. In some embodiments, the processor 120 may control the high-pressure injector 115 to inject the contrast agent into the blood vessel of the target object. In some embodiments, the contrast agent may be injected into the blood vessel of the target object manually.

The contrast agent may be injected through a vein or an artery. In some embodiments, the processor 120 may control the high-pressure injector 115 to determine an injection position of injecting the contrast agent into the blood vessel of the target object. For example, in lower extremity vascular interventions, the contrast agent may be injected in a tibial vein or femoral vein. As another example, when evaluating the condition of the entire vascular system, the contrast agent may be injected intravenously, and the contrast agent injected intravenously may be delivered throughout the entire vascular system, including the arteries and the veins, thereby providing a comprehensive vascular imaging rather than just the arteries. As yet another example, in cerebral vascular imaging, the contrast agent may be injected at an aortic arch since the contrast agent may reach the brain quickly from the aortic arch. If injected through a vein (e.g., a vein in the arm), the contrast agent may take a relatively long time to travel with the blood to the left side of the heart, into the lungs, back to the heart, and ultimately be transported to the brain. Intravenous imaging may usually show images of multiple blood vessels instead of showing only artery blood vessels.

Preferably, in the embodiment of the present disclosure, an arterial injection may be preferred since the arterial injection can avoid the non-specific problems caused by the intravenous injection and can achieve a good contrast result.

In some embodiments, the processor 120 may determine a speed, a concentration, an injection time period, an injection start/end time, an injection interval, etc., of injecting the contrast agent into the blood vessel of the target object according to a requirement to cooperate with the scanning process. For example, the processor 120 may control the high-pressure injector 115 to start to inject the contrast agent into the blood vessel of the target object at 2 seconds before a start time point of the scanning process. As another example, the processor 120 may control the high-pressure injector 115 to stop injecting the contrast agent into the blood vessel of the target object at 2 seconds before an end time point of the scanning process. More descriptions regarding the injecting the contrast agent into the blood vessel of the target object may be found below.

An injection time of the contrast agent may be determined according to an actual scanning need. For example, an injection amount or the injection time period of the contrast injection may be minimized. For example, a start time of the contrast agent injection may be earlier than a start time of the spiral scanning, and a stop time of the contrast agent injection may be earlier than a stop time of the spiral scanning. As another example, the start time of the contrast agent injection may be the same as the start time of the spiral scanning, and the stop time of the contrast agent injection may be earlier than the stop time of the spiral scanning. As yet another example, the stop time of the contrast agent injection may be earlier than the stop time of the spiral scanning. That is, in practical application, it is only necessary to ensure that during the spiral scanning, there is the contrast agent in the blood vessel of the target object. The actual injection time of the contrast agent may be determined according to demand, which is not limited in the embodiment.

In some embodiments, the imaging data is obtained through a spiral scanning manner using the radiation emitter and the radiation detector at the two ends of an arm (e.g., C-arm, O-arm) of the X-ray scanning device.

In some embodiments, the processor 120 may control the medical scanning device (e.g., the X-ray imaging device 110) to perform the spiral scanning manner during a diffusion phase or a filling phase of the contrast agent. The diffusion phase refers to a time period in which the contrast agent gradually spreads or propagates after the contrast agent is injected into the blood vessel. The filling phase refers to a time period after the contrast agent is injected into the blood vessel during which the contrast agent diffuses sufficiently into a target blood vessel to make the target blood vessel clearly visible. More descriptions regarding the medical scanning device (e.g., the X-ray imaging device 110) may be found in the relevant descriptions thereof.

The spiral scanning manner refers that the scanning process is performed at the same time with spiral movements. The spiral movements refer to a type of movement mode that combines rotations and/or forward movements of the target object. The target object may move spirally by combining the rotations and the forward movements. In the spiral scanning manner, the radiation emitter and/or the radiation detector may rotate around the target object when moving along one direction (e.g., an extension direction along a length of a scanning bed). According to the spiral scanning manner, continuous volumetric data of a scanning region may be obtained in a single imaging process.

In some embodiments, the spiral scanning manner may be implemented according to the arm. For example, the processor 120 may drive, by controlling the frame 114, the arm 111 to move along the length of the scanning bed. As another example, the processor 120 may rotate, by controlling the arm 111 to rotate around the target object or to slide along an arc of the arm, the radiation emitter 112 and the radiation detector 113 at the two ends of the arm 111.

The imaging data refers to data obtained at different angles or directions, and the imaging data reflects information about absorption and scattering of rays by tissues of the target object. For example, data obtained at a plurality of angles (e.g., on the top, at the bottom, on the side, and/or at an oblique angle) of the brain respectively that reflects information about the absorption and scattering of rays by tissues of a brain in a brain scanning process.

In some embodiments, the processor 120 may control the arm 111 to move along a first direction and the radiation emitter 112 to rotate around the first direction at the same time. The imaging data is obtained by receiving radiations emitted by the radiation emitter 112 via the radiation detector 113.

Figure 3A:
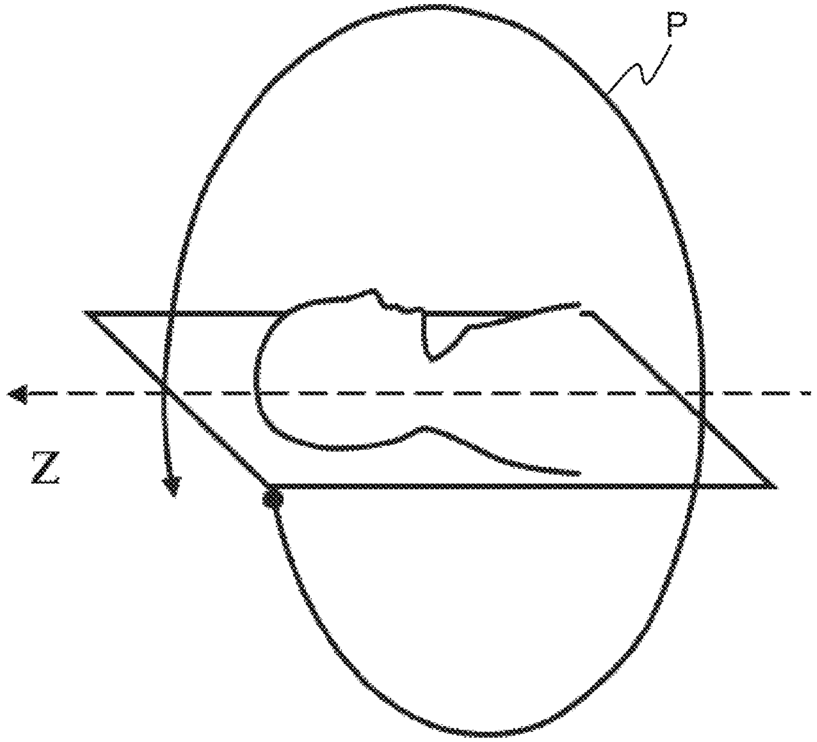
FIG. 3A is a schematic diagram of a vascular imaging method according to some embodiments of the present disclosure.
Figure 3B:
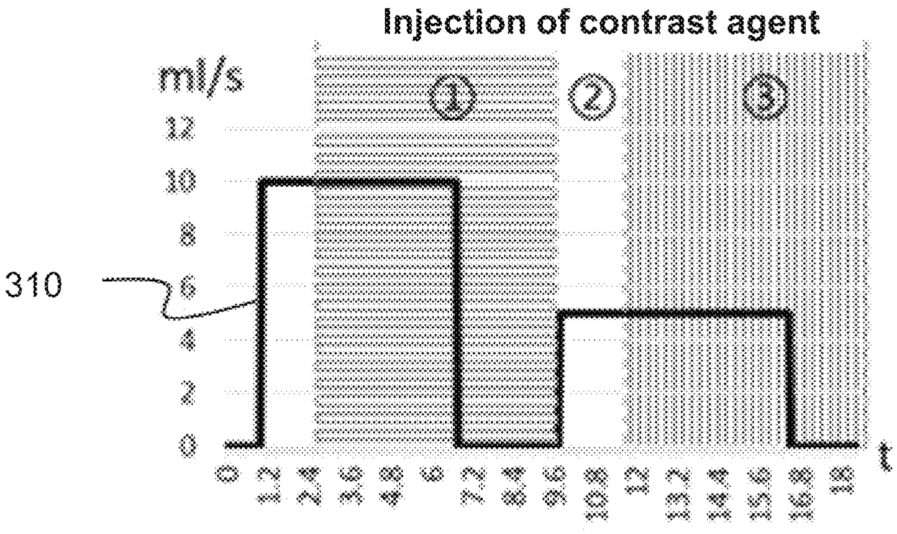
FIG. 3B is a schematic diagram of a vascular imaging method according to some embodiments of the present disclosure.
Figure 3C:
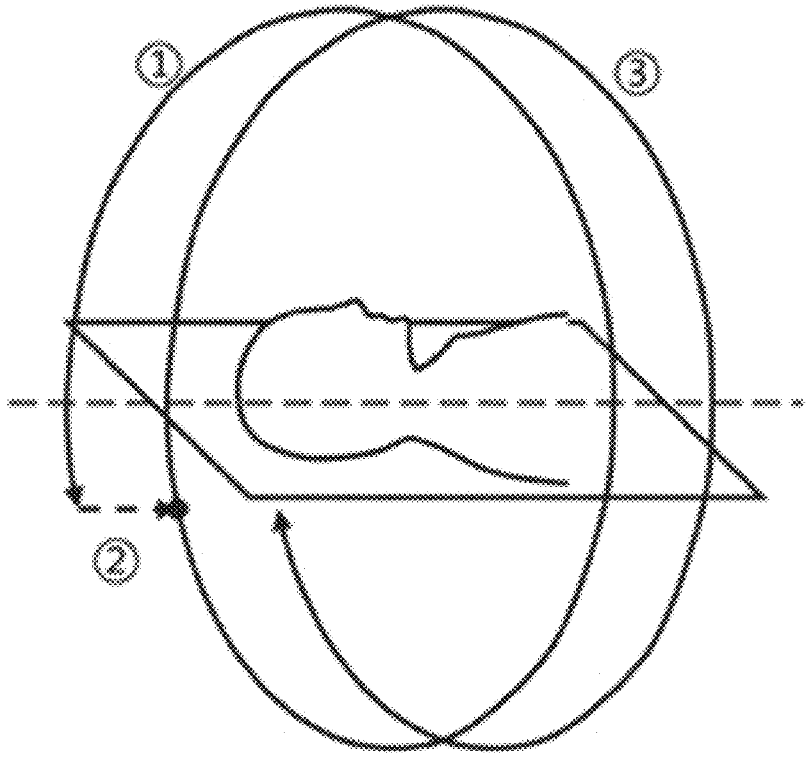
FIG. 3C is a schematic diagram of a vascular imaging method according to some embodiments of the present disclosure.

FIG. 3A~FIG. 3C are schematic diagrams of vascular imaging methods according to some embodiments of the present disclosure. The first direction refers to one of directions along the length of the scanning bed. For example, the first direction may be one of a z-axis positive direction or a z-axis negative direction in FIG. 3A. In some embodiments, the first direction may be an extension direction along the length of the scanning bed.

The rotation of the radiation emitter 112 around an axis oriented in the first direction may be a clockwise circular movement or a counterclockwise circular movement. For example, as shown in FIG. 3A, the radiation emitter 112 may be rotated in the direction indicated by a curve P or in the opposite direction of the direction indicated by the curve P.

For example, as shown in FIG. 3A, in the head and neck vascular imaging, a scan starting point may be at the aortic arch. The processor 120 may control the arm 111 to move along a direction from the foot to the head, and control the radiation emitter 112 to make a counterclockwise circular movement around an axis along the direction from the foot to the head, so that the radiation emitter 112 at one end of the arm 111 to perform the spiral scanning movement. The imaging data may be obtained by the radiation detector 113 receiving the radiations emitted by the radiation emitter 112 at several positions of a spiral scanning trajectory.

The spiral scanning manner means that the radiation emitter 112 and the radiation detector 113 at the two ends of the arm 111 scans at the same time with the spiral movements. For example, during a spiral scanning manner, the radiation emitter 112 and/or the radiation detector 113 may rotate around the target object when moving along one direction (e.g., the extension direction along the length of the scanning bed).

In some embodiments, the processor 120 may also obtain a first speed and a second speed based on a preset corresponding relationship. The processor 120 controls the arm 111 to move along the first direction at the first speed, and controls the radiation emitter 112 to rotate around the first direction at the second speed. More descriptions regarding the related content may be found in FIG. 4 and the relevant descriptions thereof.

In some embodiments, the injection of the contrast agent into the blood vessel of the target object may be performed simultaneously or alternately with the spiral scanning manner of the radiation emitter 112 and the radiation detector 113.

The injection of the contrast agent and the spiral scanning manner being performed simultaneously refers to that the injection of the contrast agent into the blood vessel of the target object and the spiral scanning manner of the radiation emitter 112 and the radiation detector 113 start and/or end at the same time. For example, at the same time that the radiation emitter 112 at one end of the arm 111 starts to rotate and emit radiations, the injection of the contrast agent into the blood vessel of the target object may start. As another example, at the same time that the radiation emitter 112 stops rotating and emitting radiations, the injection of the contrast agent into the blood vessel of the target object may end.

The injection of the contrast agent and the spiral scanning manner being performed alternately refers to that the injection of the contrast agent into the blood vessel and the spiral scanning manner do not start and/or do not end at the same time. For example, the contrast agent may be injected into the blood vessel before the spiral scanning manner starts. As another example, the injection of the contrast agent into the blood vessel may stop before the spiral scanning manner ends.

At the moment when the injection of the contrast agent starts, the contrast agent in the blood vessel may not have diffused yet, the visibility of the blood vessel may not be immediately improved, and the quality of the image obtained from the scanning at this time may not be improved. Therefore, the processor 120 may delay the spiral scanning manner. For example, the contrast agent may be injected into the blood vessel of the target object, and the spiral scanning manner may start until the contrast agent reaches a filling state.

In some embodiments, the spiral scanning manner may include at least a first sub-scanning and a second sub-scanning, and the injection of the contrast agent may include at least a first injection and a second injection. The start time of the first sub-scanning is the same as or later than the start time of the first injection of the contrast agent, and the stop time of the first sub-scanning is the same as or later than the stop time of the first injection of the contrast agent. The start time of the second sub-scanning may be the same as or later than the start time of the second injection of the contrast agent, and the stop time of the second sub-scanning may be the same as or later than the stop time of the second injection of the contrast agent. In some embodiments, there may be a time interval between the first sub-scanning and the second sub-scanning, that is, there may be a time interval between the stop time of the first sub-scanning and the start time of the second sub-scanning. In some embodiments, there may be a time interval between the first injection and the second injection, that is, there may be a time interval between the stop time of the first injection and the start time of the second injection. During at least a portion of the time interval, the spiral scanning manner may be performed, and the injection of the contrast agent is unnecessary, thereby reducing the injection amount of the contrast agent.

In some embodiments, the first injection may start at a first time point. The first time point may be determined based on an acquisition preparation time period. For example, the first injection may start when the acquisition preparation is completed. The first sub-scanning may start after a first time period of the first time point. The second injection may start at a second time point before the second sub-scanning starts. In some embodiments, a time difference between the second time point and the start time of the second sub-scanning may be equal to the first time period. In some embodiments, the first time period may be an experience value or a system default value or set after adjusting according to individual difference based on the experience value or the system default value.

For example, as shown in FIG. 3B and FIG. 3C, the processor 120 may control the high-pressure injector 115 to start to inject the contrast agent into the blood vessel at 1.2 seconds, and control the arm 111 to start the spiral scanning manner at 2.4 seconds. Furthermore, the processor 120 may control the high-pressure injector 115 to start to inject the contrast agent into the blood vessel again at 9.6 seconds, and control the arm 111 to start the spiral scanning manner again at 12 seconds. A curve 310 refers to an injection concentration curve of the contrast agent. Phase 1 (from 2.4 seconds to 9.6 seconds) is the contrast agent filling phase. Phase 2 (from 9.6 seconds to 12 seconds) is the contrast agent elimination phase. Phase 3 (a time period after 12 seconds) is the contrast agent filling phase that the contrast agent reaches the filling state again.

At a time period when the injection of the contrast agent stops, the contrast agent in the blood vessel may not fade, and the filling state may continue for a few moments. Thus, the processor 120 may control the arm 111 to continue the spiral scanning manner. For example, the spiral scanning manner may stop until the contrast agent is not in the filling state.

For example, as shown in FIG. 3B and FIG. 3C, the processor 120 may control the high-pressure injector 115 to stop injecting the contrast agent into the blood vessel at 7.2 seconds, and control the arm 111 to stop the spiral scanning manner at 9.6 seconds. Furthermore, the processor 120 may control the high-pressure injector 115 to stop injecting the contrast agent into the blood vessel again at 16.8 seconds, and control the arm 111 to stop the spiral scanning manner again at about 18 seconds.

In some embodiments of the present disclosure, the injection of the contrast agent into the blood vessel of the target object may be performed alternately with the spiral scanning manner of the radiation emitter 112 and the radiation detector 113, which helps to precisely control the scanning process at an optimal time period when the contrast agent is filled. Thus, an optimal image quality is obtained in a shortest time, the scanning efficiency and quality are improved, and a time that the patient needs to be kept in a specific position or be exposed to radiation is reduced, thereby improving the comfort and safety of the patient. At the same time, the vascular imaging method of arterial injection of the contrast agent may improve the contrast of blood vessels, reduce the injection dose of the contrast agent, make full use of the diffusion time of the contrast agent, and ensure the contrast in critical regions.

In some embodiments, the spiral scanning may be implemented in a manner that the arm of the X-ray scanning device moves, and stepping and rotation are achieved by moving the entire arm. In some embodiments, the spiral scanning may be implemented in a manner that a sliding mechanism (e.g., a slide rail) is disposed between the arm and the frame of the arm, and stepping and rotation are achieved through the sliding mechanism.

As shown in FIG. 1, the arm may rotate relative to the frame at a connection between the frame and the arm. The rotating of the arm at the connection may be understood that the frame does not move, and the arm rotates in the first direction. For example, a bearing may be disposed at the connection, and the arm may rotate relative to the frame through the bearing.

Figure 5A:
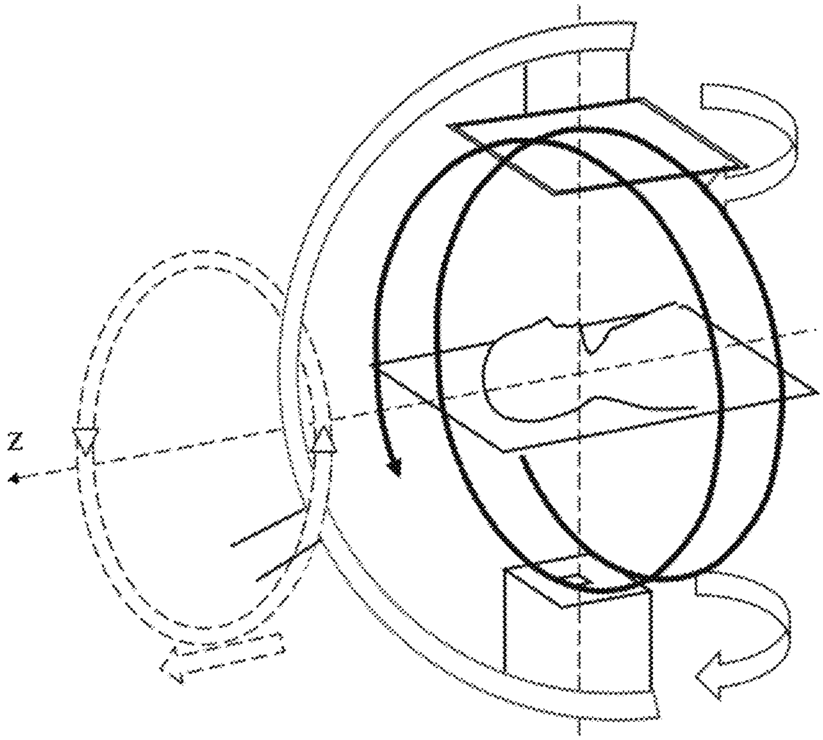
FIG. 5A is a schematic diagram of a vascular imaging method according to other embodiments of the present disclosure.

It should be noted that in FIG. 1 or FIG. 5A, the arm is in a head position. For example, a plane where the arm is located is parallel to the first direction (that is, the connection of the arm and the frame is in the axial direction of the frame). The scanning process of this design is simple to control, but a scanning depth may be limited by a radius of the arm (that is, a maximum depth of the scan range is the radius of the arm).

Figure 5B:
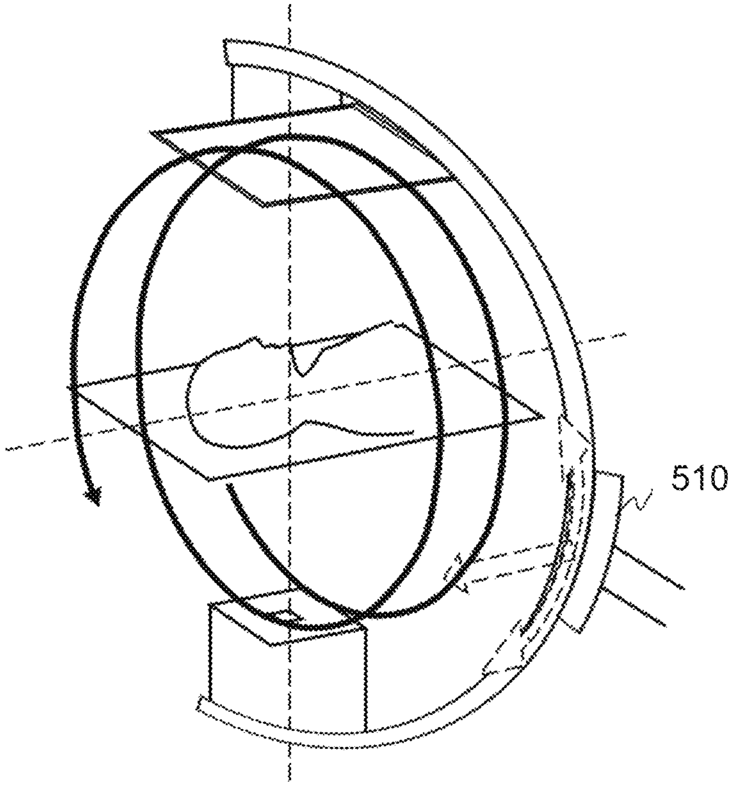
FIG. 5B is a schematic diagram of a vascular imaging method according to other embodiments of the present disclosure.

In some embodiments, the rotation of the arm may be achieved by driving the arm by the frame. FIG. 5A and FIG. 5B are schematic diagrams of vascular imaging methods according to some embodiments of the present disclosure. For example, as shown in FIG. 5A, the connection between the frame and the arm may remain stationary relative to the arm, and the frame may drive the arm to rotate. The dashed unidirectional arrow on the left side is a movement trajectory in which the frame drives the arm to move along the first direction, and the dashed circular arrow is a movement trajectory in which the connection rotates around the first direction when the frame drives the arm to rotate.

In some embodiments, the rotation of the arm may be achieved by relative sliding between the arm and the frame. The sliding may be one of ways in which the arm rotates at the connection relative to the frame. In some embodiments, the connection between the frame and the arm may be equipped with a slide rail, e.g., the slide rail 510 in FIG. 5B. The arm may slide on the slide rail to move relative to the frame. As shown in FIG. 5B, the arm may slide on the slide rail 510, and the arm may move along an arc of the arm, and drive the radiation emitter at one end of the arm to make a circular movement around a centerline to realize the spiral scanning manner.

It should be noted that the arm in FIG. 5B is in a radial position of the frame. For example, the plane in which the arm is located is perpendicular to a longitudinal central axis of the target object, and the arm may be driven by the frame to move along the first direction so as to make the spiral scanning manner to cover a larger axial range (e.g., a whole body range of the patient).

In some embodiments, the connection between the arm and the frame may be at a center position of the arm. For example, the connection is at the center position of the arm as shown in FIG. 1. The processor 120 may make the center position of the arm in the moving direction, drive the arm to move along the moving direction through the frame, and control the arm to rotate around the moving direction to rotate the radiation emitter and the radiation detector at the two ends thereof.

In some embodiments, the connection between the arm and the frame may be offset from the center position of the arm, and the radiation emitter and a radiation detector may rotate relative to the arm. For example, as shown in FIG. 5A, the connection may be below the center position of the arm and the radiation emitter and the radiation detector may rotate relative to the arm. An axis of relative rotation may be a line between a center of the radiation emitter and a center of the radiation detector.

It should be noted that the arm in FIG. 5A is in a head position, for example, a position that deviates from a central axis of the frame. For example, the plane in which the arm is located is at an angle of less than 90 degrees to the first direction. In FIG. 5A, the connection between the frame and the arm may make a circular motion along the first direction and move along the first direction. The connection between the frame and the arm may be in the head position of the scanning bed. A rotation trajectory of the connection between the frame and the arm is shown by the dashed circular arrow in FIG. 5A. Therefore, the rotation may make the arm and the frame bypass the scanning bed and the target object, which may solve the problem of insufficient depth dimension when the arm is in the head position and realize a long range of the spiral scanning manner.

Since a position of a rotation point is not the center position of the arm when the arm rotates, the relative positions of the radiation emitter and the radiation detector may be counter-deviated during the rotation. For example, the vertical dashed line shown in FIG. 5A may not be in the same plane (not intersecting) with the first direction (the axial dashed line in FIG. 5A), and the direction of the imaging data may not be inconsistent at this time. This phenomenon may be avoided by the relative rotation of the radiation emitter and the radiation detector to the arm, which ensures the consistency of the direction of the imaging data.

In 220, a vascular angiographic image is generated based on the imaging data.

The vascular angiographic image refers to an image that presents a structure, position, and/or morphology of the blood vessel of the target object. The vascular angiographic image may assist in the diagnosis and evaluation of vascular disease, abnormal dilatation, stenosis, embolization, etc. In some embodiments, the vascular angiographic image may be presented in a 3D manner.

In some embodiments, the processor 120 may obtain a reconstructed image by performing rapid reconstruction based on the imaging data, and generate the vascular angiographic image by performing a vascular segmentation on the reconstructed image.

In some embodiments, the processor 120 may obtain the reconstructed image by performing, based on the imaging data, the rapid reconstruction using a reconstruction algorithm such as Circular Feldkamp-Davis-Kress (FDK), Helical Feldkamp-Davis-Kress (FDK), Katsevich, etc. In some embodiments, the processor 120 may also obtain the reconstructed image by performing, based on the imaging data, the rapid reconstruction through filtering, back projection, etc.

In some embodiments, the processor 120 may generate the vascular angiographic image by labeling the segmented blood vessel in the reconstructed image (e.g., drawing outlines of the blood vessel in the reconstructed image).

According to the imaging data, combined with an accurate reconstruction algorithm, the 3D reconstruction of blood vessels may be completed rapidly, so that a long-range angiography result may be viewed immediately during the operation.

In the intraoperative long-axial range vascular imaging method, long-axial range vascular imaging in the aortic interventional operation of aortic coarctation or thoracoabdominal aortic aneurysm, or the lower limb vascular intervention operation may be realized, which is conducive to the comprehensive observation of vascular lesions.

It should be noted that the long-axial range involved in the embodiment of the present disclosure refers to a scan range of the imaging device being greater than an intrinsic scanning range of the imaging device. In other words, when the imaging device moves during the imaging process, the imaging range may be greater than an intrinsic scanning range of the imaging device, which may be considered that an imaging of the long-axial range is performed. In some embodiments, the long-axial range mentioned in the present disclosure may be twice a scanning range of an ordinary DSA device.

For example, when the intrinsic scanning range of the imaging device is 17-18 cm in the axial direction, if the scanning region exceeds 18 cm in the axial direction by moving the imaging device (e.g., the imaging device moves axially) during the scanning, the scanning region of the imaging may be considered to be a long-axial range.

Through the combination of angiography and spiral scanning manner, as well as the rapid reconstruction of the images, so that high contrast vascular images over a long-axis range may be achieved in a short time period, thereby efficiently providing the imaging foundation for emergency operations.

In some embodiments, the processor 120 may also obtain auxiliary imaging data, generate a two-dimensional image sequence based on the imaging data and the auxiliary imaging data, and generate the vascular angiographic image based on the two-dimensional image sequence. More descriptions regarding the related content may be found in FIG. 9 and the relevant descriptions thereof.

In the vascular imaging method provided in some embodiments of the present disclosure, the contrast of blood vessels may be improved through angiography, and clear imaging of blood vessels at all levels may be achieved. At the same time, the range of vascular imaging in the axial direction may be expanded. For example, in cerebrovascular imaging, by injecting the contrast agent at the aortic arch, the long-axial 3D range of vascular imaging from the aortic arch to the cranial roof may be obtained in a single imaging process, which helps in surgical assessment planning and navigation, and reduces the related operation time and the risk of complications caused by catheter invasion into intracranial vessels. In addition, the low specificity of intravenous injection may be avoided, the vascular 3D imaging result may have a high definition, and the preoperative CTA examination may be eliminated, which may greatly reduce the preoperative examination duration of the acute patient, thereby improving the success rate of rescue.

Figure 4:
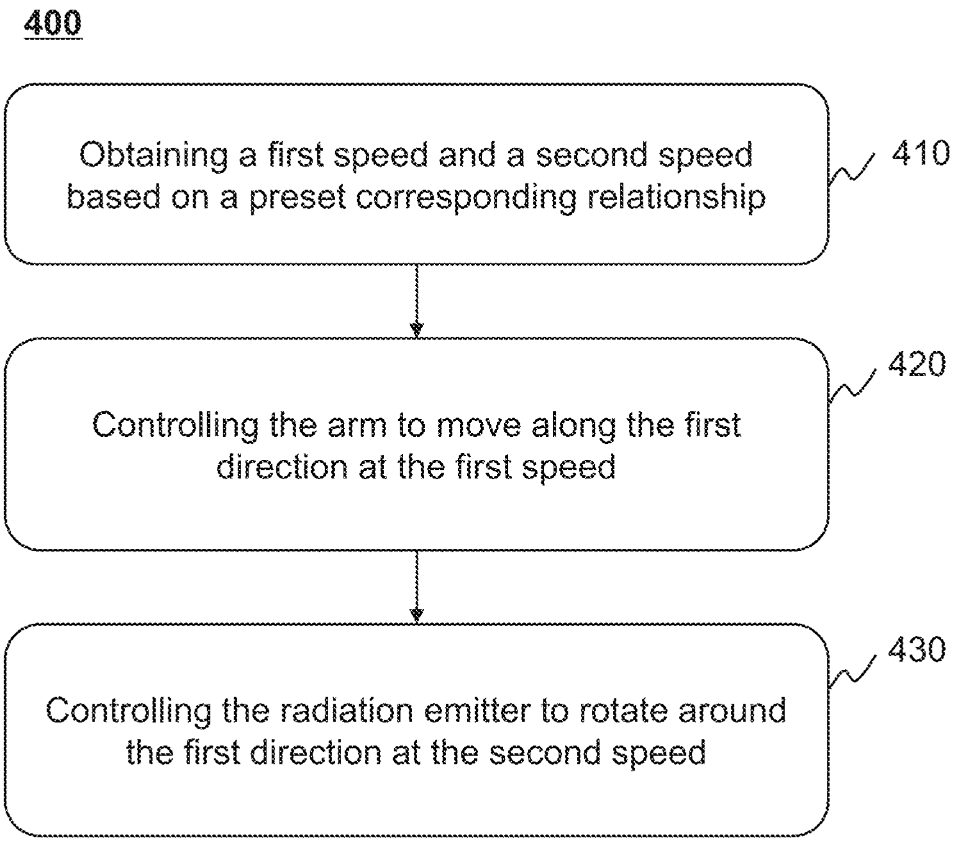
FIG. 4 is a flowchart illustrating an exemplary process for determining movement modes of an arm and a radiation emitter according to some embodiments of the present disclosure.

FIG. 4 is a flowchart illustrating an exemplary process for determining movement modes of an arm and a radiation emitter according to some embodiments of the present disclosure. In some embodiments, the process 400 may be executed by a processor (e.g., the processor 120).

In 410, a first speed and a second speed are obtained based on a preset corresponding relationship.

The preset corresponding relationship may include a mapping relationship between the first speed and the second speed that is obtained or determined in advance. In some embodiments, the preset corresponding relationship may include a mapping relationship between the first speed of the arm moving along the first direction and the second speed of the radiation emitter 112 rotating around the first direction. In some embodiments, the preset corresponding relationship may be expressed by key-value pairs, arrays, lists, dictionaries (or hash tables), sets, trees, graphs, etc., which are not limited by the embodiment.

In some embodiments, the preset corresponding relationship may be obtained according to historical data. For example, the processor 120 may construct and obtain the preset corresponding relationship by collecting a large number of actual speeds of movement of the arm moving along the axial direction during historical imaging as historical first speeds and actual speeds of rotation of the radiation emitter rotating along the radial direction during historical imaging as historical second speeds.

In some embodiments, when constructing the preset corresponding relationship, the processor 120 may also evaluate quality of a historical image (to obtain an image quality evaluation result) obtained from a historical imaging process, adjust an actual axial movement speed of the arm and/or an actual radial rotation speed of the radiation emitter during the historical imaging process (to obtain an adjustment result) according to the image quality evaluation result, and construct the preset corresponding relationship based on the adjustment result. The historical image during the historical imaging process may include a historical vascular angiographic image generated during a historical vascular imaging process.

For example, the processor 120 may adjust the actual axial movement speed of the arm and/or the actual radial rotation speed of the radiation emitter according to the image quality evaluation result. For example, the image quality evaluation result may include quality scoring parameters in a plurality of dimensions. The plurality of dimensions may include image clarity, image signal-to-noise ratio, artifact degree, blood vessel display integrity, blood vessel edge sharpness, contrast agent density, contrast, etc. The image quality evaluation result may be expressed in terms of an image quality score. If the image quality score exceeds a preset threshold, the axial movement speed and the radial rotation speed may not be adjusted. If the image quality score is less than the preset threshold, the axial movement speed and/or the radial rotation speed may be correspondingly reduced to enable more image data to be captured, thereby improving the image quality.

In some embodiments, the image quality may be determined according to a quality evaluation model. The quality evaluation model may be a machine learning model. For example, the quality evaluation model may include a convolutional neural network (CNN), a deep belief network (DBN), a regression model, or the like, or any combination thereof.

In some embodiments, the processor 120 may input the historically obtained vascular angiographic image into the quality evaluation model, and the quality evaluation model may output a corresponding image quality score. The image quality score may include scores of the vascular angiographic image in a plurality of dimensions. For example, the image quality score may include scores of the vascular angiographic image in the plurality of dimensions such as blood vessel display integrity, blood vessel edge sharpness, contrast agent density, artifact degree, contrast, etc., separately, a weighted total score of the plurality of dimensions, etc.

The quality evaluation model may be obtained by training an initial quality evaluation model with a first sample and a first label. The first sample may include a large number of sample images, and the first label may include quality scores corresponding to the sample images. In some embodiments, the first sample may be obtained according to historical data. The first label may be obtained by an expert in the art by scoring the first sample in terms of blood vessel display integrity, blood vessel edge sharpness, contrast agent density, artifact degree, contrast, etc., and labeling the first sample.

In some embodiments, the processor 120 may also adjust the actual axial movement speed of the arm and the actual radial rotation speed of the radiation emitter during the imaging process according to the image quality evaluation result. For example, a relatively low image quality score of a particular image may indicate that the scanning speed may be relatively fast during the imaging process, resulting in unclear imaging, and the actual axial movement speed of the arm and/or the actual radial rotation speed of the radiation emitter may need to be adjusted.

In some embodiments, the processor 120 may also determine an adjustment recommendation for the axial movement speed and the radial rotation speed based on a speed adjustment model. The speed adjustment model may be a machine learning model. For example, the speed adjustment model may include a convolutional neural network (CNN), a deep belief network (DBN), a regression model, or the like, or any combination thereof.

An input of the speed adjustment model may include the vascular angiographic image and the actual axial movement speed of the arm and the actual radial rotational speed of the radiation emitter corresponding to the vascular angiographic image, and an output of the speed adjustment model may include the image quality score corresponding to the vascular angiographic image and the adjustment recommendation for the axial movement speed and the radial rotation speed. The adjustment recommendation may include adjusting a direction (e.g., increasing, decreasing, remaining unchanged, etc.), adjusting a scope, etc.

The speed adjustment model may be obtained by training a second sample and a second label. The second sample may include a large number of sample images and axial movement speeds and radial rotation speeds corresponding to the sample images. The second label may include quality scores corresponding to the sample images and adjustment recommendations for the axial movement speeds and the radial rotation speeds. In some embodiments, the second sample may be obtained according to historical data, and the second label may be obtained and labeled by an expert in the art. For example, for each sample image in the second sample, the expert in the art may label the image quality and determine the adjustment recommendation for the axial movement speed and the radial rotation speed.

In some embodiments, the quality evaluation model may be a part of the speed adjustment model. In some embodiments, the quality evaluation model and the speed adjustment model may also share an image quality evaluation part.

In some embodiments, the processor 120 may adjust the axial movement speed and the radial rotation speed based on the adjustment recommendation for the axial movement speed and the radial rotation speed and construct the preset corresponding relationship.

In some embodiments, the processor 120 may determine, based on a scan plan of the target object, an axial scan range. The processor 120 may determine, based on the axial scan range, a movement mode of the arm. The processor 120 may determine, based on the movement mode of the arm, a query target from the preset corresponding relationship, and determine the first speed and the second speed based on the query target.

The scan plan refers to a scan scheme that is developed for the target object (e.g., a patient) based on medical diagnosis or treatment needs. For example, the scan plan may include parameters such as a scanning region, a resolution, a scan duration, etc.

The axial scan range refers to a region range to be scanned by the arm along the extension direction of the length of the scanning bed. It should be noted that different axial scan ranges correspond to different movement modes of the arm. For example, when the axial scan range is relatively small (e.g., smaller than 38 cm, 39 cm, 40 cm, 41 cm, 42 cm), the arm may move along one direction (e.g., the first direction) to meet the needs of the scan plan. For example, when the axial scan range is large (e.g., greater than 38 cm, 39 cm, 40 cm, 41 cm, 42 cm), the arm may need to move back and forth (e.g., moving along a certain direction from a position in the middle of the scanning region to a preset position and moving along the opposite direction) to meet the needs of the scan plan. Similarly, different arm movement modes may correspond to different rotation angles and rotation speeds of the corresponding radiation emitters. The movement mode of the arm may include a movement direction, a movement speed, a pause, a return, etc. of the arm.

In some embodiments, the axial scan range and the movement mode of the arm may be determined based on the scan plan. For example, the scan plan may include the axial scan range and the movement mode of the arm. In some embodiments, the axial scan range and the movement mode of the arm may also be automatically determined by the processor 120 based on the scan plan. For example, the processor 120 may automatically calculate the axial scan range and the movement mode of the arm according to information such as a scan range, a scanning parameter, etc., of the scan plan in conjunction with a scanning device used.

The query target refers to a query region or a query sub-table that corresponds to the scan plan of the target object in the preset corresponding relationship. In some embodiments, the preset corresponding relationship may be divided into a plurality of regions, a plurality of sub-tables, etc. One region or one sub-table may correspond to one movement mode of the arm, and the first speed and the second speed corresponding to the movement mode. The processor 120 may determine the query target by retrieving a title or header of the query region or the query sub-table, etc.

In some embodiments, the first speed and the second speed in the preset corresponding relationship may also be referred to as a reference first speed and a reference second speed, respectively. In some embodiments, the preset corresponding relationship also includes an image quality score corresponding to the reference first speed and the reference second speed. In some embodiments, the processor 120 may determine the reference first speed and the reference second speed corresponding to an image with a highest image quality score in the query target as the first speed and the second speed of the arm of the scanning device in the vascular reconstruction process.

It should be understood that since the amount of data contained in the preset corresponding relationship may be relatively large, and if the first speed and the second speed are determined by querying directly in the preset corresponding relationship, the amount of data to be processed may be very large, and the query efficiency may be relatively low. In some embodiments of the present disclosure, the query target corresponding to the scan plan may be determined based on the movement mode of the arm, and the first speed and the second speed may be determined based on the query target, which may accurately and quickly determine the first speed and the second speed, reduce the amount of data to be processed, and improve the query efficiency.

In some embodiments, the processor 120 may further determine whether the first speed or the second speed exceeds a speed threshold. In response to determining that the first speed exceeds the speed threshold or the second speed exceeds the speed threshold, the processor 120 may perform an image reconstruction using a limited-angle compensation algorithm to generate the vascular angiographic image.

The speed threshold may include a first subthreshold corresponding to the first speed and a second subthreshold corresponding to the second speed, respectively. In some embodiments, the determining whether the first speed or the second speed exceeds the speed threshold may include determining whether the first speed exceeds the first subthreshold or determining whether the second speed exceeds the second subthreshold.

In some embodiments, in response to determining that the first speed exceeds the speed threshold or the second speed exceeds the speed threshold may include: in response to determining that the first speed exceeds the first subthreshold, in response to determining that the second speed exceeds the second subthreshold, or in response to determining that the first speed exceeds the first subthreshold and the second speed exceeds the second subthreshold at the same time. That is, in response to determining that either the first speed or the second speed exceeds the speed threshold, the processor 120 may perform the image reconstruction using the limited-angle compensation algorithm to generate the vascular angiographic image.

During the arm scanning, when the first speed or second speed is too fast (e.g., exceeding the speed threshold), the imaging data obtained may be incomplete or insufficient to reconstruct a high-quality image. In addition, artifacts are prone to occur when the vascular angiographic image is generated, which may affect the quality of the image and limit its application in clinical diagnosis and treatment. With the limited-angle compensation algorithm, the incomplete image data caused by the too-fast movement of the device or the limited scanning angle during the imaging process may be solved, and the quality of the generated vascular angiographic image may be restored or improved to a certain degree, thereby providing assistance for clinical diagnosis.

In some embodiments, during the process of obtaining the imaging data through the spiral scanning manner using the radiation emitter and radiation detector at the two ends of the arm, if the first speed of the arm moving along the first direction or the second speed of the radiation emitter rotating around the first direction exceeds the speed threshold, the processor 120 may perform the image reconstruction using the limited-angle compensation algorithm to generate the vascular angiographic image. More descriptions regarding the generating the vascular angiographic image may be found in the relevant sections above, such as the operation 220.

The numerical values of the first speed and the second speed in the preset corresponding relationship may reflect whether the limited-angle compensation is required to a certain extent. Therefore, it may be possible to directly annotate whether the image reconstruction needs to be performed on each first speed and each second speed in the preset corresponding relationship based on the limited-angle compensation algorithm. In some embodiments, other suitable image reconstruction algorithms may also be given in the preset corresponding relationship.

Therefore, the processor 120 may also directly determine, based on the preset corresponding relationship, whether to perform the image reconstruction based on the limited-angle compensation algorithm.

In some embodiments of the present disclosure, when the spiral movement speed of the arm is too fast or the amount of data obtained by scanning is insufficient, the image reconstruction may be performed using the limited-angle compensation algorithm, which may improve the quality of the generated vascular angiographic images, thereby providing assistance for clinical diagnosis.

In some embodiments, the preset corresponding relationship may further include a mapping relationship between the first speed of the arm moving along the first direction, the second speed of the radiation emitter rotating around the first direction, and an injection time of the contrast agent. The injection time of the contrast agent may include an injection start time, an injection end time, an injection time period, etc. In some embodiments, when the contrast agent needs to be injected into the blood vessel of the target object for multiple times, the injection time may also include a start time, an end time, and a time period of each injection of the multiple injections.

In some embodiments, the processor 120 may also determine, based on the preset corresponding relationship, the injection time of the contrast agent into the blood vessel of the target object, and inject the contrast agent into the blood vessel of the target object according to the injection time.

By presetting the mapping relationship between the injection time of the contrast agent, the first speed of the arm moving along the first direction, and the second speed of the radiation emitter rotating around the first direction, the injection time of the contrast agent may be determined, thereby avoiding an increase in scan duration caused by the waiting of the injection of the contrast agent and improving the scanning efficiency.

In some embodiments, the injection time may be related to the axial scan range and the movement mode of the arm. For example, the greater the axial scan range is, the longer the injection time may be. As another example, when there is a pause and return in the movement of the arm, the injection of the contrast agent may also need to be paused accordingly. That is, the contrast agent may need to be injected in multiple times in this case.

In some embodiments, the mapping relationship between the first speed of the arm moving along the first direction, the second speed of the radiation emitter rotating around the first direction, and the injection time of the contrast agent may be determined based on historical data. For example, a large number of first speeds, second speeds, and injection times of the contrast agent during historical imaging processes may be collected. The mapping relationship between the first speed, the second speed, and the injection time of the contrast agent may be determined through data analysis, machine learning model prediction, etc.

For example, the mapping relationship between the first speed, the second speed, and the injection time of the contrast agent may be determined based on an injection time determination model. The injection time determination model may be a machine learning model. For example, the injection time determination model may include a convolutional neural network (CNN), a deep belief network (DBN), a regression model, or the like, or any combination thereof.

An input of the injection time determination model may include the vascular angiographic image, the axial scan range, and the movement mode of the arm, and an output of the injection time determination model may include the injection time.

The injection time determination model may be obtained by training a third sample and a third label. The third sample may include a large number of sample images and axial scan ranges and movement modes of the arm corresponding to the sample images. The third label may include injection times corresponding to the sample images. In some embodiments, the third sample may be obtained according to historical data, and the third label may be labeled and obtained by an expert in the art.

In some embodiments of the present disclosure, the injection time of the contrast agent into the blood vessel of the target object may be determined based on the preset corresponding relationship. The distribution of the contrast agent is optimized and help to ensure a preferred concentration and distribution state of the contrast agent in the blood vessel, thereby improving the clarity and contrast of the imaging process. At the same time, the injection time and dose of the contrast agent may also be controlled, which may ensure the quality of the imaging process and reduce the amount of contrast agent used at the same time, thereby improving the efficiency of the scanning and reducing the discomfort of the patient.

In 420, the arm is controlled to move along the first direction at the first speed.

In some embodiments, the arm may be connected to the frame, and the processor 120 may drive the arm through the frame to move along the first direction at the first speed.

In 430, the radiation emitter is controlled to rotate around the first direction at the second speed.

In some embodiments, the rotation of the radiation emitter around the first direction at the second speed may be realized by the rotation of the arm. For example, when the arm rotates, the radiation emitter disposed at one end of the arm may be moved with the rotation of the arm, thereby realizing the rotation around the first direction at the second speed.

In some embodiments of the present disclosure, by controlling the arm to move along the first direction at the first speed, and by controlling the radiation emitter to rotate around the first direction at the second speed, the processor may reasonably control the amount of imaging data obtained and the distribution of the scan duration, so that the subsequently generated vascular angiographic image has a high quality and may meet the needs of clinical medical diagnosis.

Figure 6:
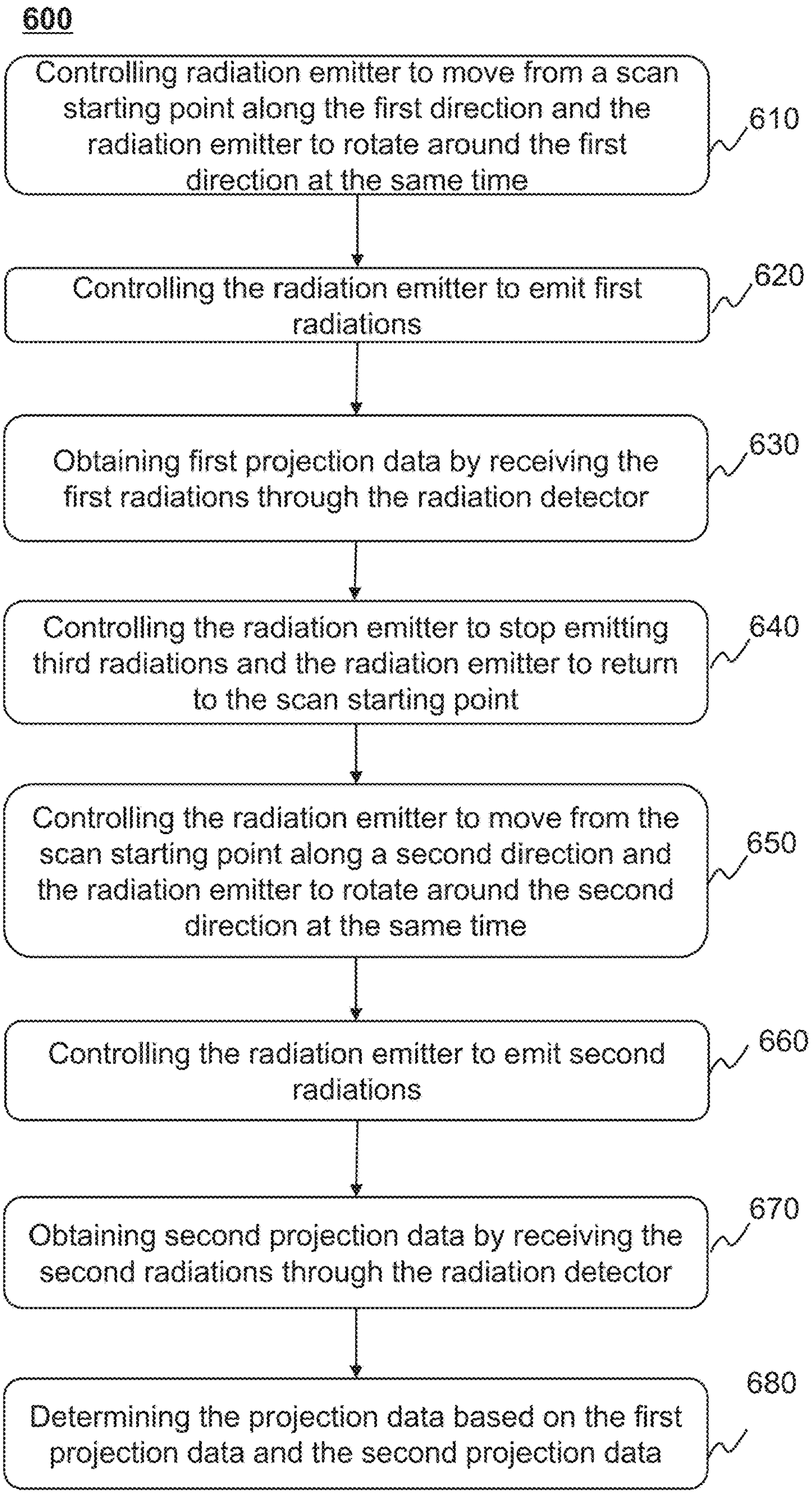
FIG. 6 is a flowchart illustrating an exemplary process for obtaining imaging data according to other embodiments of the present disclosure.

FIG. 6 is a flowchart illustrating an exemplary process for obtaining imaging data according to some embodiments of the present disclosure. In some embodiments, the process 600 may be configured to implement the operation 220 of the process 200 to obtain the imaging data through a spiral scanning manner using a radiation emitter and a radiation detector at two ends of an arm. In some embodiments, the process 600 may be executed by the processor 120. As shown in FIG. 6, the process 600 may include the following operations.

In 610, an radiation emitter is controlled to move from a scan starting point along a first direction, and the radiation emitter is controlled to rotate around the first direction at the same time.

The scan starting point refers to a starting position of the spiral scanning manner. The scan starting point may be expressed in terms of a position of a surface and/or an interior of the target object, a position of the radiation emitter and/or a position of the radiation detector, etc. For example, the scan starting point may be a mouth or an aortic arch. As another example, the scan starting point is a position where the radiation emitter is located directly above a midpoint of the scanning bed and/or the radiation detector is located directly below the midpoint of the scanning bed.

In some embodiments, the processor 120 may select an endpoint or a non-endpoint (a point between the endpoints in the scanning region) of the scanning region as the scan starting point. For example, an endpoint of the scanning region, a center point of the scanning region, a golden section position within the scanning region, etc., may be selected as the scan starting point. In some embodiments, the scan starting point may be determined based on scanning needs. For example, in a single head and neck vascular imaging process, one endpoint of the scanning region (e.g., the aortic arch) may be designated as the scan starting point. As another example, in secondary head and neck vascular imaging process, the center point of the scanning region (approximately the mouth) may be designated as the scan starting point.

For example, as shown in FIGS. 3B and 3C, in phase ①, the contrast agent in the blood vessel may be in the filling state, and the processor 120 may control the radiation emitter to move from the scan starting point (e.g., the mouth) along the first direction (e.g., a foot-to-head direction) and the radiation emitter to rotate (e.g., in a counterclockwise circle) around the first direction at the same time.

In 620, the radiation emitter is controlled to emit first radiations.

The processor 120 may control the radiation emitter to emit the first radiations and rotate around the first direction at the same time. The first radiations refer to radiations emitted from the radiation emitter when the first imaging data is obtained.

In some embodiments, the first radiations may be emitted when the radiation emitter is controlled to move in the first direction and rotate around the first direction.

In 630, the first imaging data is obtained by receiving the first radiations through the radiation detector.

The processor 120 may receive the first radiations emitted from the radiation emitter through the radiation detector and obtain the first imaging data based on the first radiations.

In 640, the radiation emitter is controlled to stop emitting the first radiations and the radiation emitter is controlled to return to the scan starting point.

For example, as shown in FIG. 3C, in phase ②, the contrast agent in the blood vessel may be in the elimination state, the radiation emitter and the radiation emitter may return to the scan starting point, and the radiation emitter may not emit the third radiations in this process.

In 650, the radiation emitter is controlled to move from the scan starting point along a second direction and the radiation emitter may be controlled to rotate around the second direction at the same time.

The second direction refers to a direction opposite to the first direction in the length direction of the scanning bed. For example, in FIG. 3A, the first direction is the z-axis positive direction, and the second direction is the z-axis negative direction. In some embodiments, due to the limited rotational angle of the X-ray imaging device e.g., along a single direction (e.g., a clockwise direction), the arm may not rotate continuously for multiple turns. Therefore, by setting the two rotation directions to be opposite (e.g., using a bidirectional spiral scanning manner), imaging data over a long axial range may be obtained.

For example, as shown in FIGS. 3B and 3C, in phase ③, the contrast agent in the blood vessel may be again in the filling state, and the radiation emitter may be controlled to rotate from the scan starting point (e.g., the mouth) along the second direction (e.g., the head-to-foot direction) and the radiation emitter may be controlled to rotate (e.g., in a clockwise circle) around the second direction at the same time.

In some embodiments, the scan starting point is a non-endpoint position in the scan range, for example, a position of a point between two endpoints in the scan range.

In 660, the radiation emitter is controlled to emit second radiations.

The processor 120 may control the radiation emitter to emit the second radiations and rotate around the second direction at the same time. The second radiations refer to radiations emitted from the radiation emitter when second imaging data is obtained.

In some embodiments, the second radiations may be emitted when the radiation emitter is controlled to move in the second direction and rotate around the second direction.

In 670, the second imaging data is obtained by receiving the second radiations through the radiation detector.

The processor 120 may receive the second radiations emitted from the radiation emitter through the radiation detector and obtain the second imaging data based on the second radiations.

It should be noted that the first imaging data and the second imaging data have one same scan starting point, so the first imaging data and the second imaging data may together form continuous spiral trajectory imaging data.

A bidirectional spiral scanning trajectory with the non-endpoint as the scan starting point may avoid the problem of scan duration waste caused by the inability of the radiation emitter to rotate continuously for multiple circles in some cases or the problem of dose waste and poor reconstruction effect caused by the non-continuous spiral of the trajectory, which may make full use of the contrast agent diffusion time and ensure the contrast in critical regions.

In 680, the imaging data is determined based on the first imaging data and the second imaging data.

In some embodiments, the processor 120 may obtain the imaging data by splicing the first imaging data and the second imaging data.

It should be noted that the process shown in the process 600 may be considered as one scan or a partial scan within one scan. For example, the scan range that needs to be scanned by one scan may be divided into a plurality of sub-scopes, and the operations shown in the process 600 may be performed on each sub-scope.

Figure 7:
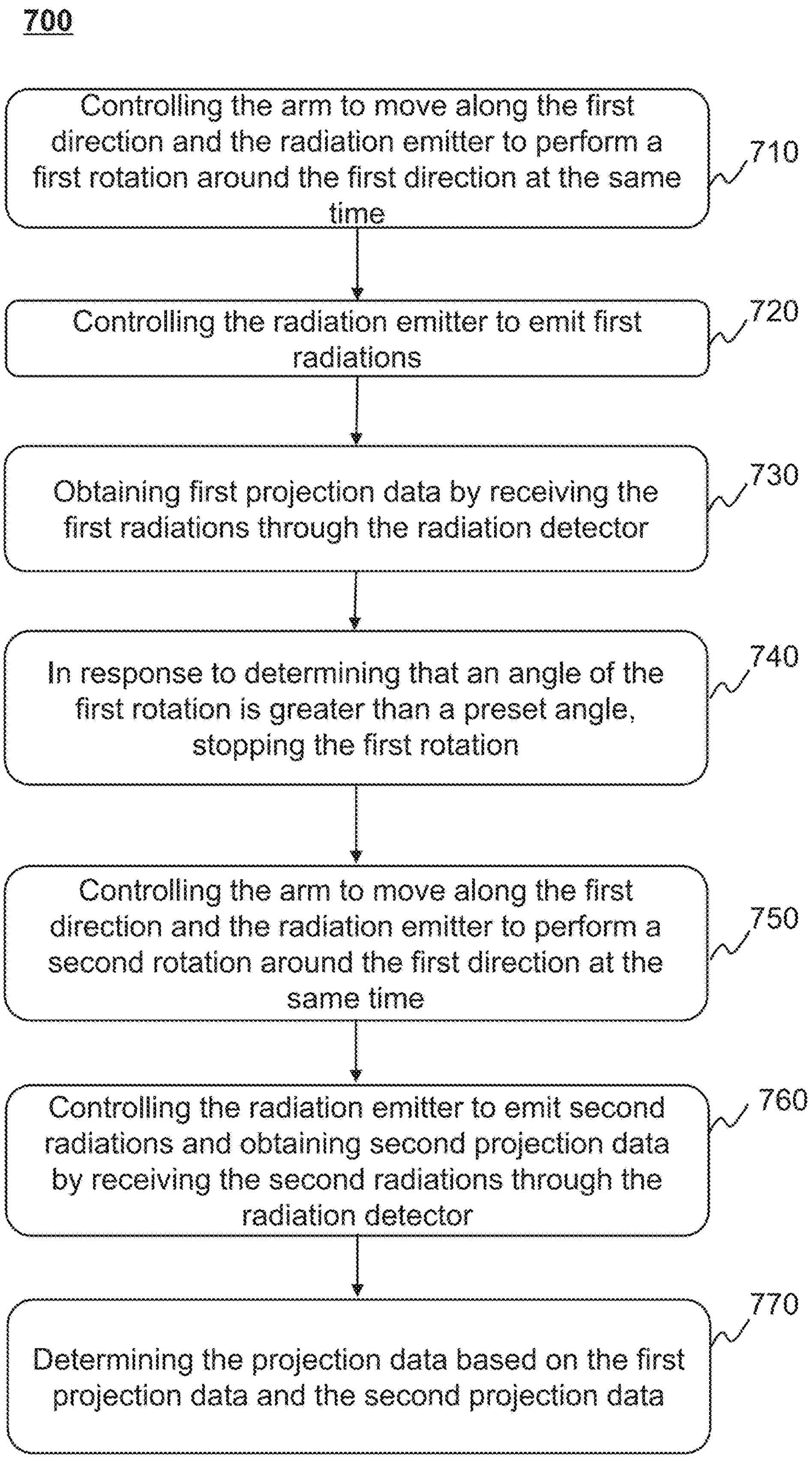
FIG. 7 is a flowchart illustrating an exemplary process for obtaining imaging data according to yet other embodiments of the present disclosure.

FIG. 7 is a flowchart illustrating an exemplary process for obtaining imaging data according to yet other embodiments of the present disclosure. In some embodiments, the process 700 may be configured to implement the operation 220 of the process 200 to obtain the imaging data through a spiral scanning manner using a radiation emitter and a radiation detector at two ends of an arm. In some embodiments, the process 700 may be executed by the processor 120. As shown in FIG. 7, the process 700 may include the following operations.

In 710, the arm is controlled to move along a first direction and the radiation emitter may be controlled to perform a first rotation around the first direction at the same time.

Figure 8:
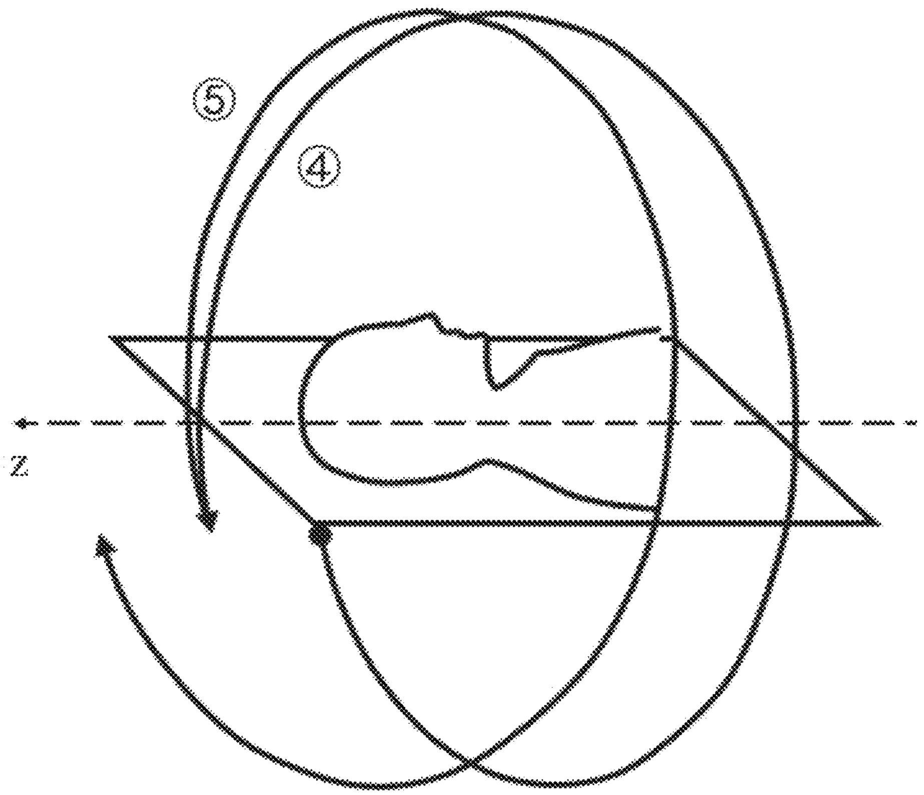
FIG. 8 is a schematic diagram of a vascular imaging method according to yet other embodiments of the present disclosure.

FIG. 8 is a schematic diagram of a vascular imaging process according to some embodiments of the present disclosure. For example, as shown in FIG. 8, at the start of the scan process, the processor 120 may control the arm to move along a first direction (the z-axis positive direction in FIG. 8) while controlling the radiation emitter to perform a first rotation around the first direction.

In 720, the radiation emitter is controlled to emit first radiations.

The processor 120 may control the radiation emitter to emit the first radiations and perform the first rotation around the first direction at the same time. The first radiations refer to radiations emitted from the radiation emitter when first imaging data is obtained.

In some embodiments, the first radiations may be emitted when the radiation emitter is controlled to move in the first direction and rotate around the first direction.

In 730, the first imaging data is obtained by receiving the first radiations through the radiation detector.

The processor 120 may receive the first radiations from the radiation emitter through the radiation detector and obtain the first imaging data based on the first radiations.

For example, as shown in FIG. 8, in phase ④, the radiation emitter may emit the first radiations, and the radiation emitter may rotate counterclockwise from the scan starting point to make a circular movement and move along the z-axis positive direction at the same time. And the first imaging data may be obtained by receiving the first radiations emitted from the radiation emitter through the radiation detector. A high-pressure injector may be controlled to inject the contrast agent before the start of phase ④ and to stop injecting the contrast agent before the end of phase ④.

In 740, in response to determining that an angle of the first rotation is greater than a preset angle, the first rotation is stopped.

When the radiation emitter is rotated to the preset angle, the processor 120 may control the radiation emitter to stop emitting the first radiations and stop the first rotation, and control the arm to stop moving along the first direction. The preset angle may be a maximum angle that the arm may rotate, for example, 200 degrees, 400 degrees, etc. The preset angle may also be a preferred angle determined empirically, for example, 180 degrees, 360 degrees, etc.

In 750, the arm is controlled to move along the first direction and the radiation emitter is controlled to perform a second rotation around the first direction at the same time.

A rotation direction of the second rotation may be opposite to a rotation direction of the first rotation. In some embodiments, an ending point position of the first rotation may be a starting point position of the second rotation.

For example, as shown in FIG. 8, in phase ⑤, the processor 120 may control the radiation emitter to make a circular movement in an opposite direction of phase ④ to from an ending point of the rotation in phase ④, and control the arm to continue to move along the z-axis positive direction at the same time.

For example, the direction represented by phase ④ corresponds to the first rotation, which is rotated counterclockwise, and the direction represented by phase ⑤ corresponds to the second rotation, which is rotated clockwise.

In 760, the radiation emitter is controlled to emit second radiations, and the second imaging data is obtained by receiving the second radiations through the radiation detector.

In some embodiments, the second radiations may be emitted when the radiation emitter is controlled to move in the second direction and rotate around the second direction.

Continuing to refer to FIG. 8, in phase ⑤, the processor 120 may control the radiation emitter to emit the second radiations and obtain the second imaging data by receiving the second radiations emitted from the radiation emitter through the radiation detector.

In some embodiments, the processor 120 may also control the high-pressure injector to inject the contrast agent before the start of phase ⑤ and to stop injecting the contrast agent before the end of phase ⑤.

It should be noted that the scan ending point of phase ④ is the same as the scan starting point of phase ⑤, so the first imaging data obtained in phase ④ and the second imaging data obtained in phase ⑤ may also form the continuous spiral trajectory imaging data.

In 770, the imaging data is determined based on the first imaging data and the second imaging data.

In some embodiments, the processor 120 may obtain the imaging data by splicing the first imaging data and the second imaging data.

It should be noted that the above description of the determining the imaging data based on the first imaging data and the second imaging data is merely an example.

In some embodiments, the processor 120 may divide the scan range into a plurality of subranges, determine a local scan starting point (e.g., a midpoint of the subrange) of each subrange, and obtain, by performing the operations shown in FIG. 3B and FIG. 3C on the each subrange, a plurality of sets of local imaging data. Each set of local imaging data may include local first imaging data and local second imaging data. The scanning module 520 may obtain the imaging data by splicing together the plurality of sets of local imaging data.

In some cases, the arm may have a limited angle of continuous rotation, and the arm may need to be reset between two or more scanning processes. By pausing the injection of the contrast agent between scanning processes, the amount of the contrast agent may be reduced. By injecting the contrast agent in advance before each scanning process, the scan duration period may coincide with the contrast agent filling time period, which may maximize the use of the filling time of the contrast agent and obtain a long-range continuous spiral scanning image with a limited rotation angle of the arm.

Figure 9:
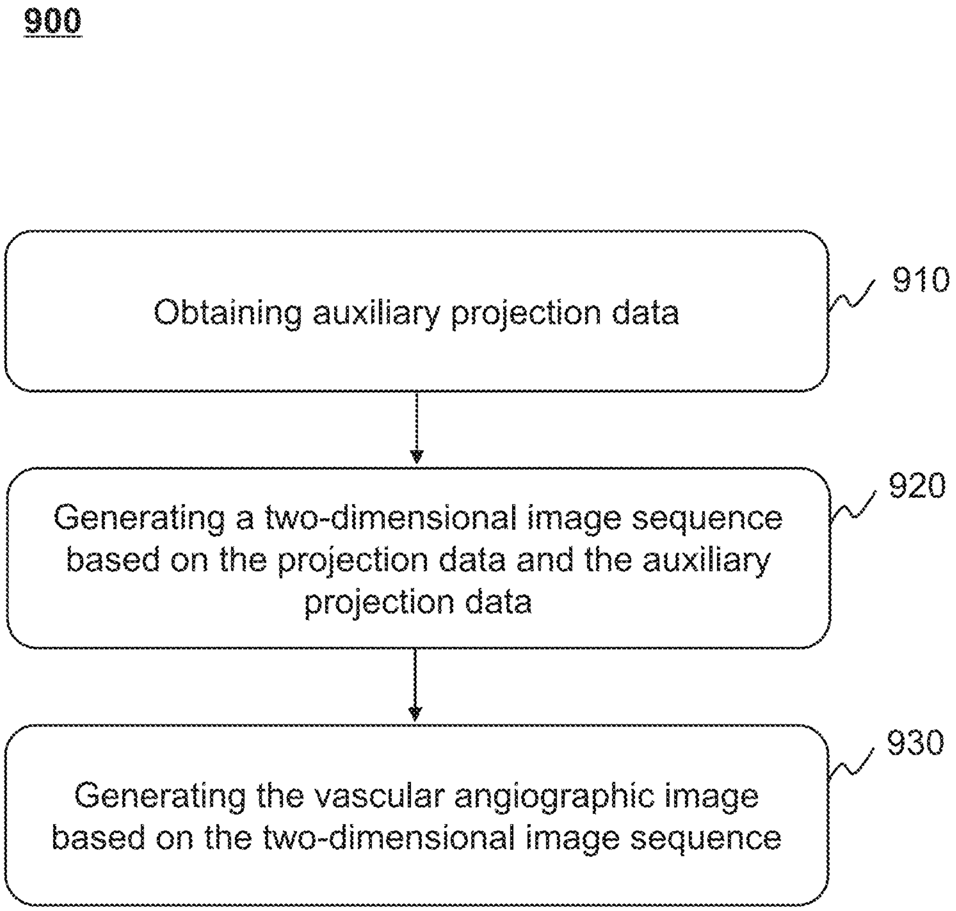
FIG. 9 is a flowchart illustrating an exemplary process for generating a vascular angiographic image based on imaging data according to other embodiments of the present disclosure.

FIG. 9 is a flowchart illustrating an exemplary process for generating a vascular angiographic image based on imaging data according to some embodiments of the present disclosure. In some embodiments, if the vascular angiographic image generated in the operation 220 does not meet a preset condition and/or a clinical need, the vascular angiographic image may need to be regenerated. The preset condition may include a contrast between the blood vessel and surrounding tissues in the vascular angiographic image being larger than a preset threshold (e.g., 5%). The preset threshold may be manually adjusted when the image is viewed. The blood vessel may be segmented based on the vascular angiographic image. The clinical need may include that the vascular angiographic image considered by the physician to clearly show the vascular structure, etc. In some embodiments, the process 900 may be executed by a processor (e.g., the processor 120). As shown in FIG. 9, the process 900 may include the following operations.

In 910, auxiliary imaging data is obtained.

The auxiliary imaging data refers to imaging data of the target object that is collected without injection of a contrast agent. The auxiliary imaging data may reflect preliminary information about the target object. The contrast of the blood vessel may be relatively low since there is no enhancement effect of the contrast agent.

In some embodiments, the processor 120 may obtain the auxiliary imaging data through a manner same as and/or similar to that of the operation 220.

In 920, a two-dimensional image sequence is generated based on the imaging data and the auxiliary imaging data.

In some embodiments, the processor 120 may generate the two-dimensional image sequence by performing digital subtraction on the imaging data and the auxiliary imaging data. The imaging data refers to imaging data obtained through the spiral scanning manner (e.g., operation 210 in FIG. 2).

The digital subtraction refers to an image processing manner in which the auxiliary imaging data is subtracted from the imaging data. The vascular structure in the imaging data may become more visible due to the presence of the contrast agent, and the tissues and/or organs surrounding the blood vessels in the imaging data may be the same as or similar to those in the auxiliary imaging data. Therefore, the auxiliary imaging data may be subtracted from the imaging data through mathematical operation, and an image that shows only the blood vessel filled with the contrast agent may be obtained.

The two-dimensional image sequence refers to a collection of a plurality of 2D images. The plurality of 2D images refer to 2D vascular subtraction images of a plurality of positions and/or angles of the target object.

In some embodiments, the processor 120 may obtain the 2D vascular subtraction image corresponding to each piece of imaging data by performing digital subtraction on each piece of imaging data and corresponding auxiliary imaging data, and designate the 2D vascular subtraction images as the two-dimensional image sequence.

In 930, the vascular angiographic image is generated based on the two-dimensional image sequence.

In some embodiments, the processor 120 may generate the vascular angiographic image based on the two-dimensional image sequence through a reconstruction algorithm (e.g., Circular FDK, Helical FDK, Katsevich, etc.), filtering, back projection, etc.

The process 900 may be used as a backup solution in the event that the quality of the vascular angiographic image generated through the operation 220 is poor, which provides a reliable image base for surgery.

It should be noted that the foregoing descriptions of the processes 200, 400, 600, 700, 900, etc., are merely provided for the purposes of example and illustration, and not intended to limit the scope of application of the present disclosure. For those skilled in the art, various corrections and changes may be made to the processes 200, 400, 600, 700, 900, and 1000 under the guidance of the present disclosure. However, these corrections and changes remain within the scope of the present disclosure.

Figure 10:
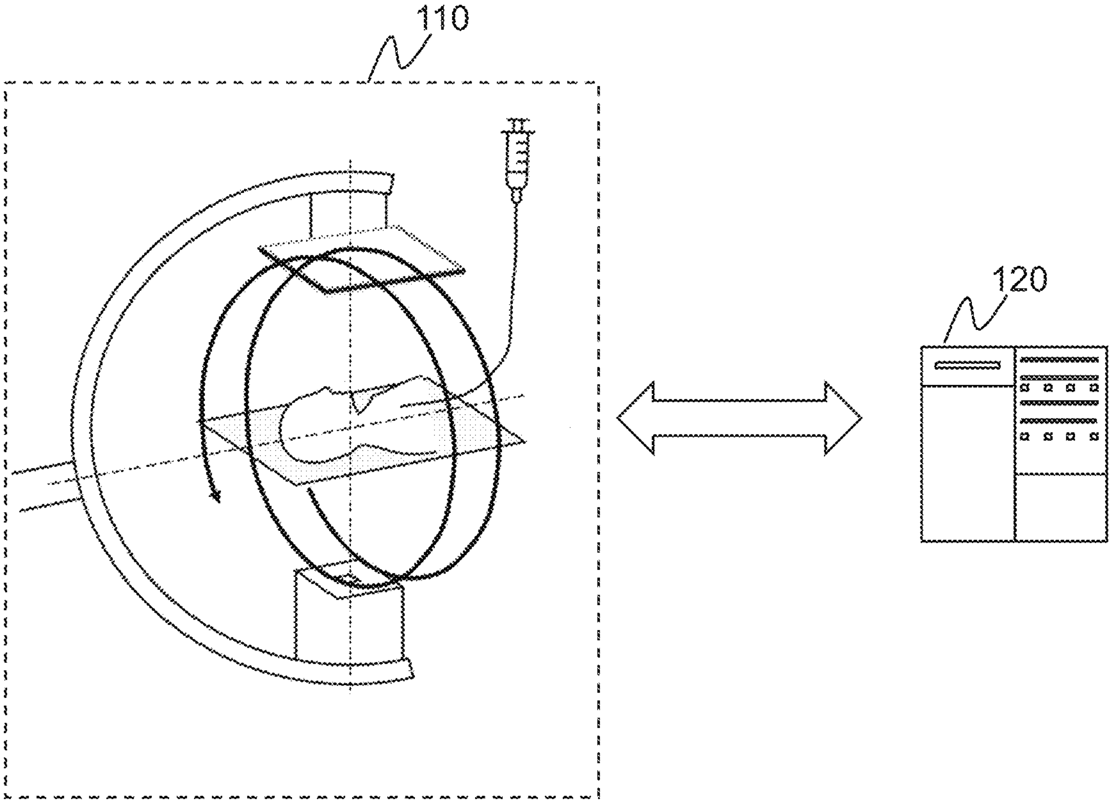
FIG. 10 is a flowchart illustrating an exemplary vascular imaging method according to some embodiments of the present disclosure.
Figure 11:
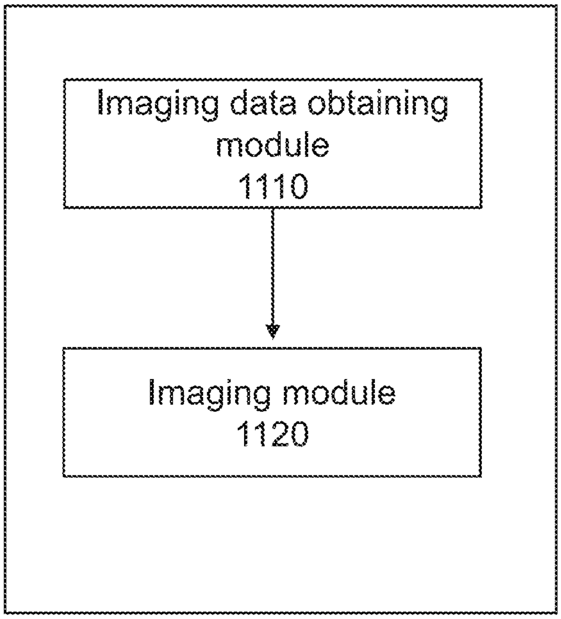
FIG. 11 is a schematic diagram illustrating an exemplary vascular imaging system according to some embodiments of the present disclosure.

FIG. 10 is a schematic diagram of a vascular imaging system according to some embodiments of the present disclosure. As shown in FIG. 11, the vascular imaging system 1000 may include an X-ray imaging device 110 and a processor 120.

The X-ray imaging device 110 may include an arm (e.g., a C-shaped arm, an O-shaped arm) and a contrast agent injection device. In some embodiments, the contrast agent injection device may include a high-pressure injector.

The processor 120 may be configured to control the contrast agent injection device to inject a contrast agent into a blood vessel of a target object. The processor 120 may obtain imaging data through a spiral scanning manner using the radiation emitter and the radiation detector at two ends of the arm, and generate a vascular angiographic image based on the imaging data.

In some embodiments, the processor 120 may be further configured to control the radiation emitter to rotate around a first direction and the arm to move along the first direction at the same time, and obtain the imaging data by receiving radiations emitted from the radiation emitter using the radiation detector.

In some embodiments, the processor 120 may be further configured to obtain a first speed and a second speed based on a preset corresponding relationship, control the arm to move along the first direction at the first speed, and control the radiation emitter to rotate around the first direction at the second speed.

In some embodiments, the processor 120 may be further configured to control the arm to move along the first direction and control the radiation emitter to perform a first rotation around the first direction at the same time, control the radiation emitter to emit first radiations, and obtain first imaging data by receiving the first radiations emitted from the radiation emitter through the radiation detector. In some embodiments, the processor 120 may be further configured to control the arm to move along the first direction and control the radiation emitter to perform a second rotation around the first direction at the same time, control the radiation emitter to emit second radiations, and obtain second imaging data by receiving the second radiations emitted from the radiation emitter through the radiation detector. A rotation direction of the second rotation may be opposite to a rotation direction of the first rotation. The processor 120 may be further configured to determine the imaging data based on the first imaging data and the second imaging data.

In some embodiments, the processor 120 may be further configured to control the arm to move from a scan starting point along the first direction and control the radiation emitter to rotate around the first direction at the same time, control the radiation emitter to emit first radiations, and obtain first imaging data by receiving the first radiations emitted from the radiation emitter through the radiation detector. In some embodiments, the processor 120 may be further configured to control the radiation emitter to stop emitting third radiations and the arm to return to the scan starting point, control the arm to move from the scan starting point along a second direction and control the radiation emitter to rotate around the second direction at the same time, control the radiation emitter to emit second radiations, and obtain second imaging data by receiving the second radiations emitted from the radiation emitter through the radiation detector. The first direction and the second direction may be opposite. The processor 120 may be further configured to determine the imaging data based on the first imaging data and the second imaging data.

It should be noted that the above descriptions of the vascular imaging system 1100 and modules thereof are merely provided for the convenience of description, and not intended to limit the present disclosure to the scope of the embodiments. It is understood that for those skilled in the art, after understanding the principle of the system, it may be possible to arbitrarily combine the various modules to form a sub-system to connect with the other modules without departing from the principle. In some embodiments, the modules may be different modules in one system, or one module that implements the functions of two or more of the modules. For example, each module may share one storage module, or each module may have its own storage module. Such deformations are within the scope of protection of the present disclosure.

FIG. 11 is a schematic diagram illustrating an exemplary vascular imaging system according to some embodiments of the present disclosure. As shown in FIG. 11, the system 1100 may include an imaging data obtaining module 1110 configured to obtain imaging data of a target object including a contrast agent. The imaging data is obtained through a spiral scanning manner. The system 1100 may further include an imaging module 1120 configured to generate a vascular angiographic image based on the imaging data. More descriptions regarding the modules in FIG. 11 may be found in the flowcharts.

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements and amendments to the present disclosure. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various parts of this specification are not necessarily all referring to the same embodiment. In addition, some features, structures, or features in the present disclosure of one or more embodiments may be appropriately combined.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

In some embodiments, the numbers expressing quantities or properties used to describe and claim certain embodiments of the present disclosure are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the present disclosure disclosed herein are illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A vascular imaging method performed via digital subtraction angiography (DSA), comprising:
- obtaining target imaging data of a target object including a contrast agent, the target imaging data being obtained through a spiral scanning manner; and
- generating a vascular angiographic image based on the target imaging data, wherein the vascular imaging method is applied to a DSA device, the DSA device includes an arm, a radiation emitter, and a radiation detector respectively disposed at two ends of the arm, the vascular imaging method further comprising:
- controlling the arm to move along the first direction at a first speed and the radiation emitter to rotate around the first direction at a second speed at the same time; and
- obtaining the target imaging data by receiving radiations emitted by the radiation emitter through the radiation detector;

the generating the vascular angiographic image based on the target imaging data includes:
- determining whether the first speed or the second speed exceeds a speed threshold; and
- in response to determining that the first speed or the second speed exceeds the speed threshold, performing an image reconstruction using a limited-angle compensation algorithm to generate the vascular angiographic image.

2. The vascular imaging method of claim 1, wherein the obtaining the target imaging data includes:
- controlling the arm to move along the first direction and the radiation emitter to perform a first rotation around the first direction at the same time;
- controlling the radiation emitter to emit first radiations;
- obtaining first imaging data by receiving the first radiations through the radiation detector;
- in response to determining that an angle of the first rotation is greater than a preset angle, stopping the first rotation;
- controlling the arm to move along the first direction and the radiation emitter to perform a second rotation around the first direction at the same time;
- controlling the radiation emitter to emit second radiations;
- obtaining second imaging data by receiving the second radiations through the radiation detector, wherein a rotation direction of the second rotation is opposite to a rotation direction of the first rotation; and
- determining the target imaging data based on the first imaging data and the second imaging data.

3. The vascular imaging method of claim 2, wherein
an ending point position of the first rotation is a starting point position of the second rotation.

4. The vascular imaging method of claim 1, wherein the obtaining the target imaging data through the spiral scanning manner using the radiation emitter and the radiation detector at the two ends of the arm includes:
- controlling the arm to move from a scan starting point along a first direction and the radiation emitter to rotate around the first direction at the same time;
- controlling the radiation emitter to emit first radiations;
- obtaining first imaging data by receiving the first radiations through the radiation detector;
- controlling the radiation emitter to stop emitting the first radiations and the arm to return to the scan starting point;
- controlling the arm to move from the scan starting point along a second direction and the radiation emitter to rotate around the second direction at the same time;
- controlling the radiation emitter to emit second radiations;
- obtaining second imaging data by receiving the second radiations through the radiation detector, wherein the first direction and the second direction are opposite; and determining the target imaging data based on the first imaging data and the second imaging data.

5. The vascular imaging method of claim 4, wherein the scan starting point is a non-endpoint position in a scan range.

6. The vascular imaging method of claim 1, wherein the arm is connected to a frame, and the frame drives the arm to move; a rotation of the arm is achieved through at least one of:

the arm rotating at a connection relative to the frame; or the connection between the frame and the arm remaining stationary relative to the arm, and the frame driving the arm to rotate.

7. The vascular imaging method of claim 6, wherein the arm rotating at the connection relative to the frame includes:

a bearing being disposed at the connection, and the arm rotating relative to the frame through the bearing; or the connection between the frame and the arm being equipped with a slide rail, and the arm sliding relative to the frame along the slide rail.

8. The vascular imaging method of claim 6, wherein the connection between the arm and the frame is at a center position of the arm; or the connection between the arm and the frame is offset from the center position of the arm, and the radiation emitter and the radiation detector rotate relative to the arm.

9. The vascular imaging method of claim 1, wherein the movement of the radiation emitter is achieved through at least one of:

drive the frame to move the arm; or the arm being equipped with a slide rail, and the slide rail moving relative to the arm.

10. The vascular imaging method of claim 1, wherein the injection of the contrast agent into a blood vessel of the target object is performed simultaneously or alternately with the spiral scanning manner of the radiation emitter and the radiation detector.

11. The vascular imaging method of claim 10, wherein the injection of the contrast agent into the blood vessel of the target object being performed alternately includes:

the spiral scanning time period of the spiral scanning partially overlapping with the injection time period of the contrast agent.

12. The vascular imaging method of claim 10, wherein the spiral scanning manner includes at least a first sub-scanning and a second sub-scanning, and injection of the contrast agent includes at least a first injection and a second injection; wherein a start time of the first sub-scanning is later than a start time of the first injection, and an end time of the first sub-scanning is later than an end time of the first injection; and a start time of the second sub-scanning is later than a start time of the second injection, and an end time of the second sub-scanning is later than an end time of the second injection.

13. The vascular imaging method of claim 1, wherein the generating the vascular angiographic image based on the target imaging data includes:

obtaining a reconstructed image by performing reconstruction based on the target imaging data; and generating the vascular angiographic image by performing a vascular segmentation on the reconstructed image.

14. The vascular imaging method of claim 1, wherein the generating the vascular angiographic image based on the target imaging data includes:

obtaining auxiliary imaging data;

generating an image sequence based on the target imaging data and the auxiliary imaging data; and generating the vascular angiographic image based on the image sequence.

15. The vascular imaging method of claim 1, wherein an axial scanning range of the spiral scanning manner is greater than 42 cm.

16. A vascular imaging system, the vascular imaging system includes an arm, a radiation emitter, and a radiation detector respectively disposed at two ends of the arm, and at least one processor configured to perform operations including:

obtaining target imaging data of a target object including a contrast agent, the target imaging data being obtained through a spiral scanning manner, including:

controlling the arm to move from a scan starting point along a first direction and the radiation emitter to rotate around the first direction at the same time;

controlling the radiation emitter to emit first radiations;

obtaining first imaging data by receiving the first radiations through the radiation detector;

controlling the radiation emitter to stop emitting the first radiations and the arm to return to the scan starting point;

controlling the arm to move from the scan starting point along the second direction and the radiation emitter to rotate around the second direction at the same time;

controlling the radiation emitter to emit second radiations;

obtaining second imaging data by receiving the second radiations through the radiation detector, wherein the second rotation is opposite to the first rotation; and determining the target imaging data based on the first imaging data and the second imaging data; and generating a vascular angiographic image based on the target imaging data.

17. A non-transitory computer-readable storage medium comprising executable instructions that, when read by at least one processor, cause the at least one processor to perform a vascular imaging method, the vascular imaging method including:

obtaining target imaging data of a target object including a contrast agent, the target imaging data being obtained through a spiral scanning manner;

generating a vascular angiographic image based on the target imaging data;

wherein the obtaining the target imaging data includes:

controlling the arm to move from a scan starting point along a first direction and the radiation emitter to rotate around the first direction at the same time;

controlling the radiation emitter to emit first radiations;

obtaining first imaging data by receiving the first radiations through the radiation detector;

controlling the radiation emitter to stop emitting the first radiations and the arm to return to the scan starting point;

controlling the arm to move from the scan starting point along a second direction and the radiation emitter to rotate around the second direction at the same time;

controlling the radiation emitter to emit second radiations;

obtaining second imaging data by receiving the second radiations through the radiation detector, wherein the first direction and the second direction are opposite; and determining the target imaging data based on the first imaging data and the second imaging data.

* * * * *